(12) United States Patent
Fischer et al.

(10) Patent No.: US 8,604,068 B2
(45) Date of Patent: Dec. 10, 2013

(54) INSECTICIDAL COMPOSITIONS OF 2-CYANOBENZENE SULFONAMIDE COMPOUNDS AND ISOMERIC FORMS THEREOF HAVING IMPROVED EFFECT

(75) Inventors: Reiner Fischer, Monheim (DE); Bernd Alig, Königswinter (DE); Christian Arnold, Langenfeld (DE); Rolf Pontzen, Leichlingen (DE); Klaus-Helmut Müller, Düsseldorf (DE)

(73) Assignee: Bayer CropScience AG, Monheim (DE)

( * ) Notice: Subject to any disclaimer, the term of this patent is extended or adjusted under 35 U.S.C. 154(b) by 505 days.

(21) Appl. No.: 12/600,425

(22) PCT Filed: May 21, 2008

(86) PCT No.: PCT/EP2008/004041
§ 371 (c)(1),
(2), (4) Date: Nov. 16, 2009

(87) PCT Pub. No.: WO2008/145282
PCT Pub. Date: Dec. 4, 2008

(65) Prior Publication Data
US 2010/0160396 A1 Jun. 24, 2010

(30) Foreign Application Priority Data

May 25, 2007 (DE) .......................... 10 2007 024 575

(51) Int. Cl.
*A01N 43/80* (2006.01)
*A01N 37/34* (2006.01)
*A01N 37/12* (2006.01)
*A01N 37/44* (2006.01)
*A61K 31/425* (2006.01)
*A61K 31/275* (2006.01)
*C07C 213/00* (2006.01)
*C07C 215/00* (2006.01)
*C07F 9/02* (2006.01)
*C07F 5/02* (2006.01)

(52) U.S. Cl.
USPC ........... 514/373; 514/524; 514/538; 564/281; 568/9

(58) Field of Classification Search
USPC .......................... 514/373, 524, 538; 564/281
See application file for complete search history.

(56) References Cited

U.S. PATENT DOCUMENTS

| | | | |
|---|---|---|---|
| 2,842,476 A | 7/1958 | Schreiber et al. | |
| 4,343,747 A | 8/1982 | Ryu et al. | |
| 4,492,705 A | 1/1985 | Drabek | |
| 4,698,358 A | 10/1987 | Drabek | |
| 4,760,076 A | 7/1988 | Drabek | |
| 4,786,650 A | 11/1988 | Drabek | |
| 4,844,734 A | 7/1989 | Iwasaki et al. | |
| 4,888,049 A | 12/1989 | Iwasaki et al. | |
| 5,164,179 A | 11/1992 | Hioki et al. | |
| 5,462,912 A | 10/1995 | Hioki et al. | |
| 5,538,937 A | 7/1996 | Hasebe et al. | |
| 5,705,476 A | 1/1998 | Hoffarth | |

(Continued)

FOREIGN PATENT DOCUMENTS

| | | |
|---|---|---|
| CA | 1162071 A1 | 2/1984 |
| DE | 3 544 436 A1 | 6/1986 |

(Continued)

OTHER PUBLICATIONS

Replace (http://www.ucpallc.com/ucpallc/ PDFs/Adjuvants/Replace_Label.pdf, 2004).*
AGROW, "Crop Protection R&D Tracking & Analysis," *Agrow Intelligence*, No. 542, p. 22 (May 2008).
Bauer, P. et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51: 131-152, Wiley and Sons, England (1997).
English language Abstract of Japanese Patent Publication No. JP 01-319467 A (1989).
English language Abstract of Japanese Patent Publication No. JP 02-006496 B2 (1990).

(Continued)

*Primary Examiner* — Sreeni Padmanabhan
*Assistant Examiner* — Uma Ramachandran
(74) *Attorney, Agent, or Firm* — Sterne, Kessler, Goldstein & Fox P.L.L.C.

(57) ABSTRACT

The present invention comprises 2-cyanobenzenesulfonic acid amides of the formula (I) and isomeric forms thereof (I-A) and (I-B)

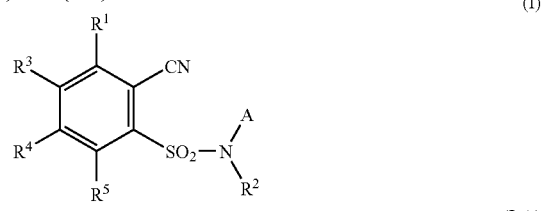

(I)

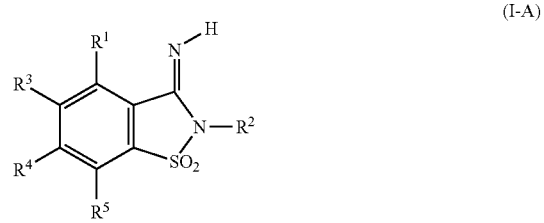

(I-A)

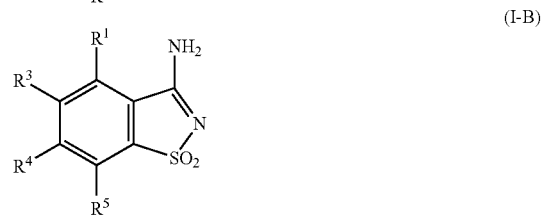

(I-B)

wherein
$R_1$, $R_2$, $R_3$, $R_4$, $R_5$ and A have the aforesaid meaning for the control of animal pests with the use of penetration enhancers and/or ammonium or phosphonium salts.

11 Claims, No Drawings

(56) References Cited

U.S. PATENT DOCUMENTS

| | | |
|---|---|---|
| 5,792,755 A | 8/1998 | Sagenmuller et al. |
| 6,602,823 B1 | 8/2003 | Rochling et al. |
| 6,645,914 B1 | 11/2003 | Woznica et al. |
| 8,017,554 B2 * | 9/2011 | Pohlman et al. ............... 504/100 |
| 2001/0055604 A1 * | 12/2001 | Kalder et al. ................. 424/405 |
| 2003/0224939 A1 | 12/2003 | Miles |
| 2004/0157743 A1 | 8/2004 | Rosenfeldt et al. |
| 2005/0009880 A1 | 1/2005 | Cottrell et al. |
| 2005/0096386 A1 | 5/2005 | Cottrell et al. |
| 2010/0167922 A1 * | 7/2010 | Pohlman et al. ............... 504/100 |

FOREIGN PATENT DOCUMENTS

| | | |
|---|---|---|
| EP | 0 033 984 A1 | 8/1981 |
| EP | 0 036 106 A2 | 9/1981 |
| EP | 0 086 748 A1 | 8/1983 |
| EP | 0 110 829 A2 | 6/1984 |
| EP | 0 133 418 A2 | 2/1985 |
| EP | 0 138 762 A1 | 4/1985 |
| EP | 0 191 734 A2 | 8/1986 |
| EP | 0 207 891 A1 | 1/1987 |
| EP | 0 453 086 A2 | 10/1991 |
| EP | 0 664 081 A2 | 7/1995 |
| EP | 0 681 865 A2 | 11/1995 |
| FR | 2600494 A1 | 6/1987 |
| JP | 01-319467 A | 12/1989 |
| JP | 02-006496 B2 | 2/1990 |
| WO | WO 92/16108 A1 | 10/1992 |
| WO | WO 95/17817 A1 | 7/1995 |
| WO | WO 98/35553 A1 | 8/1998 |
| WO | WO 00/35278 A1 | 6/2000 |
| WO | WO 02/098230 A2 | 12/2002 |
| WO | WO 2005/035486 A1 | 4/2005 |
| WO | WO 2005/055719 A1 | 6/2005 |
| WO | WO 2006/056433 A2 | 6/2006 |
| WO | WO 2006/100271 A1 | 9/2006 |
| WO | WO 2006/100288 A2 | 9/2006 |
| WO | WO 2006/124606 * | 11/2006 |
| WO | WO 2007/060220 A2 | 5/2007 |
| WO | WO 2007113119 * | 10/2007 |
| WO | WO 2008/031712 A2 | 3/2008 |
| WO | WO 2008/090048 A2 | 7/2008 |
| WO | WO 2008/145261 A1 | 12/2008 |
| WO | WO 2009/092590 A2 | 7/2009 |
| WO | WO 2009/141305 A1 | 11/2009 |

OTHER PUBLICATIONS

English language Abstract of European Patent Publication No. EP 0138762 A1 (1985).

English language Abstract of German Patent Publication No. DE 3544436 A1 (1986).

English language Abstract of European Patent Publication No. EP 0207891 A1 (1987).

International Search Report for International Application No. PCT/EP2008/004041, European Patent Office, Netherlands, mailed on Nov. 11, 2008.

\* cited by examiner

INSECTICIDAL COMPOSITIONS OF 2-CYANOBENZENE SULFONAMIDE COMPOUNDS AND ISOMERIC FORMS THEREOF HAVING IMPROVED EFFECT

The invention relates to the improvement of the action of pesticides, in particular of 2-cyanobenzenesulfonamide compounds of the formula (I), isomeric forms thereof (I-A) and (I-B), in which the variables $R^1$ to $R^5$ are defined as in claim 2, and/or agriculturally useful salts thereof through the addition of ammonium or phosphonium salts and optionally penetration enhancers, and the corresponding agents, processes for the production thereof and their use in plant protection, in particular as insecticides and/or acaricides. The present invention further relates to the use of compounds (I), (I-A) or (I-B) and/or salts thereof through the addition of ammonium or phosphonium salts for the control of animal pests, agricultural compositions, which contain a pesticidally effective quantity of at least one compound of the general formula I, (I-A) or (I-B) and/or of at least one agriculturally useful salt of I, (I-A) or (I-B) and of at least one inert liquid and/or solid agriculturally acceptable carrier and at least one penetration enhancer and/or ammonium or phosphonium salts, and a method for the control of animal pests, wherein the animal pests, their environment, their breeding grounds, their nutrition source, the plant, the seeds, the soil, the area, the substance or the environment in which the animal pests grow or can grow, or the substances, plants, seeds, soils, areas or spaces which are to be protected against infestation or contamination with the animals are treated with a pesticidally effective quantity of at least one 2-cyanobenzenesulfonamide compound of the general formula (I), (I-A) or (I-B) and/or at least one agriculturally acceptable salt thereof.

Animal pests destroy standing and harvested crops and attack wooden buildings and structures, as a result of which they cause major economic losses in food production and to property. Although a large number of pesticidal agents are known, there is still a demand for new agents for the control of animal pests, since the pests to be controlled can develop resistance to these agents. In particular, animal pests such as insects and spider mites are difficult to control effectively.

EP 0033984 describes substituted 2-cyanobenzenesulfonamide compounds with aphicidal activity. The benzenesulfonamide compounds preferably bear a fluorine atom or chlorine atom in the 3 position of the phenyl ring. Also known in WO 2005/035486 and WO 2006/056433 were 2-cyanobenzenesulfonamides with insecticidal action. Their use for soil and seed applications is described in WO2006/100271 and WO 2006/100288. In addition, isomeric forms of the 2-cyanobenzenesulfonamides and derivatives of the isomeric forms and their insecticidal action are also described in EP 86748, EP 110829, EP 133418, EP 138762, DE 3544436, EP 191734, EP 207891, JP 1989/319467 and JP 1990/006496. Further, 2-cyanobenzenesulfonamides are described in WO 2007/060220 and WO 2008/031712. Reference is hereby expressly made to these publications.

All the active substances contained in the agents according to the invention are already known and can be produced by processes described in the state of the art (see references cited above). Their pesticidal action is good, but not always completely satisfactory, particularly at low application doses and concentrations. There is therefore a need for an increase in the activity of the pesticides containing the compounds.

The target of the present invention are therefore agents and methods for the improvement of the activity of compounds of the general formula (I), (I-A) and (I-B), in particular against insects and spider mites, which are difficult to control.

In the literature, it has already been stated that the action of various active substances can be increased by addition of ammonium salts. However, these are salts with detergent action (e.g. WO 95/017817) or salts with longer alkyl and/or aryl substituents which have a permeabilizing action or increase the solubility of the active substance (e.g. EP-A 0 453 086, EP-A 0 664 081, FR-A 2 600 494, U.S. Pat. Nos. 4,844,734, 5,462,912, 5,538,937, U.S.-A 03/0224939, U.S.-A 05/0009880, U.S.-A 05/0096386). Further, the state of the art describes the action only for certain active substances and/or certain uses of the agents in question. In yet other cases, they are salts of sulfonic acids, with which the acids themselves have a paralyzing action on insects (U.S. Pat. No. 2,842,476). An increase in activity e.g. due to ammonium sulfate is for example described for the herbicides glyphosate and phosphinothricin (U.S. Pat. No. 6,645,914, EP-A2 0 036 106). A corresponding action with insecticides is neither disclosed nor rendered obvious by this state of the art.

The use of ammonium sulfate as a formulation additive is also described for certain active substances and uses (WO 92/16108), but there it serves for stabilization of the formulation, not for increasing the activity.

It has now entirely surprisingly been found that the action of insecticides and/or acaricides of the 2-cyanobenzenesulfonamide class (I) and isomeric forms thereof (I-A) and (I-B) can be markedly increased by the addition of ammonium or phosphonium salts to the application solution or through the incorporation of these salts into a formulation containing 2-cyanobenzenesulfonamides (I), and isomeric forms thereof (I-A) and (I-B). A subject of the present invention is thus the use of ammonium or phosphonium salts for increasing the action of pesticides that contain insecticidally and/or acarcidallly active 2-cyanobenzenesulfonamides (I) and isomeric forms thereof (I-A) and (I-B) as the active substance. Also a subject of the invention are agents which contain insecticidally active 2-cyanobenzenesulfonamides (I) and isomeric forms thereof (I-A) and (I-B) and ammonium or phosphonium salts increasing their action, namely both formulated active substances and also ready-for-use agents (sprays). Finally, a further subject of the invention is the use of these agents for the control of noxious insects and/or spider mites.

The 2-cyanobenzenesulfonamide compounds (I) and isomeric forms thereof (I-A) and (I-B) are described by the general formulae

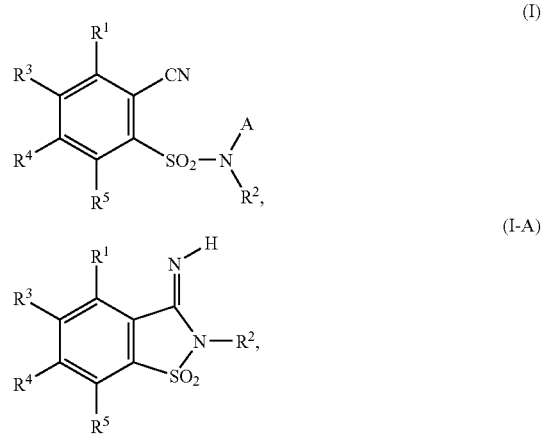

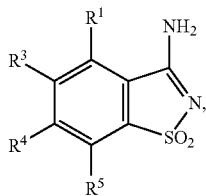

in which
A stands for hydrogen, $C_1$-$C_6$ alkyl or $C_2$-$C_6$ alkenyl
$R^1$ stands for hydrogen, halogen, $C_1$-$C_4$ alkyl, $C_1$-$C_4$ haloalkyl, $C_1$-$C_4$ alkoxy or $C_1$-$C_4$ halo-alkoxy;
$R^2$ stands for hydrogen, $C_1$-$C_6$ alkyl, $C_2$-$C_6$ alkenyl, $C_2$-$C_6$ alkynyl, $C_3$-$C_8$ cycloalkyl or $C_1$-$C_4$ alkoxy, where the five last-named residues can be unsubstituted, partly or completely halogenated and/or can bear one, two or three residues from the group $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_1$-$C_4$ alkylcarbonyl, $C_1$-$C_4$ alkoxycarbonyl, cyano, amino, ($C_1$-$C_4$ alkyl)amino, di-($C_1$-$C_4$ alkyl)amino, $C_3$-$C_8$ cycloalkyl and phenyl, wherein the phenyl can be unsubstituted, partly or completely halogenated and/or can bear one, two or three substituents from the group $C_1$-$C_4$ alkyl, $C_1$-$C_4$ haloalkyl, $C_1$-$C_4$ alkoxy or $C_1$-$C_a$ haloalkoxy;
$R^3$, $R^4$ and $R^5$ mutually independently stand for hydrogen, halogen, cyano, nitro, $C_1$-$C_6$ alkyl, $C_3$-$C_8$ cycloalkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_2$-$C_6$ alkenyl, $C_2$-$C_6$ alkynyl, $C_1$-$C_4$ alkoxycarbonyl, amino, ($C_1$-$C_4$ alkyl)amino, di-($C_1$-$C_4$ alkyl)amino, aminocarbonyl, ($C_1$-$C_4$ alkyl)aminocarbonyl and di-($C_1$-$C_4$ alkyl)aminocarbonyl.

Here compounds of the formula (I) in which A stands for hydrogen can optionally be present in the isomeric form (I-A); compounds of the formula (I) in which A and $R^2$ stand for hydrogen can optionally be present in the isomeric form (I-B).

The compounds of the formula (I) and isomeric forms thereof (I-A) and (I-B) have a broad insecticidal and/or acaricidal action, but in specific cases the action leaves something to be desired.

The active substances can be used in the compositions according to the invention in a broad concentration range. However, the concentration of the active substances in the formulation is usually 0.1-50 wt. %.

Ammonium and phosphonium salts which according to the invention increase the action of pesticides containing 2-cyanobenzenesulfonamides and isomeric forms thereof (I-A) and (I-B) are defined by formula (II)

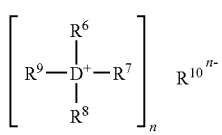

in which
D stands for nitrogen or phosphorus,
D preferably stands for nitrogen,
$R^6$, $R^7$, $R^8$ and $R^9$ mutually independently stand for hydrogen or each for optionally substituted $C_1$-$C_8$ alkyl or singly or multiply unsaturated, optionally substituted $C_1$-$C_8$ alkylene, wherein the substituents can be selected from halogen, nitro and cyano,
$R^6$, $R^7$, $R^8$ and $R^9$ preferably mutually independently stand for hydrogen or each stand for optionally substituted $C_1$-$C_4$ alkyl, wherein the substituents can be selected from halogen, nitro and cyano,
$R^6$, $R^7$, $R^8$ and $R^9$ particularly preferably mutually independently stand for hydrogen, methyl, ethyl, n-propyl, i-propyl, n-butyl, i-butyl, s-butyl or t-butyl,
$R^6$, $R^7$, $R^8$ and $R^9$ quite especially preferably stand for hydrogen,
n stands for 1, 2, 3 or 4,
n preferably stands for 1 or 2,
$R^{10}$ stands for an inorganic or organic anion,
$R^{10}$ preferably stands for hydrogen carbonate, tetraborate, fluoride, bromide, iodide chloride, monohydrogen phosphate, dihydrogen phosphate, hydrogen sulfate, tartrate, sulfate, nitrate, thiosulfate, thiocyanate, formate, lactate, acetate, propionate, butyrate, pentanoate, citrate or oxalate,
$R^{10}$ particularly preferably stands for lactate, sulfate, monohydrogen phosphate, dihydrogen phosphate, nitrate, thiosulfate, thiocyanate, citrate, oxalate or formate.
$R^{10}$ quite especially preferably stands for sulfate.

The ammonium and phosphonium salts of the formula (II) can be used over a broad concentration range for increasing the action of pesticides containing 2-cyanobenzenesulfonamides and/or isomeric forms thereof. In general, the ammonium or phosphonium salts are used in the ready-for-use pesticide at a concentration of 0.5 to 80 mmol/l, preferably 0.75 to 37.5 mmol/l, particularly preferably 1.5 to 25 mmol/l. In the case of a formulated product, the ammonium and/or phosphonium salt concentration in the formulation is selected so that after dilution of the formulation to the desired active substance concentration it lies in these stated general, preferred or particularly preferred ranges. The concentration of the salt in the formulation here is usually 1-50 wt. %.

In a preferred embodiment of the invention, not only an ammonium and/or phosphonium salt, but also in addition a penetration enhancer, is added to the pesticides to increase the activity. It must be described as entirely surprising that even in these cases a still further increase in activity is to be observed. Hence also a subject of the present invention is the use of a combination of penetration enhancers and ammonium and/or phosphonium salts for increasing the activity of pesticides which contain acaricidally/insecticidally active 2-cyanobenzenesulfonamides and/or isomeric forms thereof (I-A) and (I-B) as the active substance. Also a subject of the invention are agents which contain insecticidally active 2-cyanobenzenesulfonamides and/or isomeric forms thereof (I-A) and (I-B), penetration enhancers and ammonium and/or phosphonium salts, namely both formulated active substances and also ready-for-use agents (sprays). Finally, also a subject of the invention is the use of these agents for the control of noxious insects.

Possible penetration enhancers in the present connection are all those substances which are normally used in order to improve the penetration of agrochemical active substances in plants. In this connection, penetration enhancers are defined by the fact that they penetrate from the aqueous spray and/or the spray deposit into the cuticle of the plant and thereby are able to increase the mobility of active substances in the cuticle. The method described in the literature (Baur et al., 1997, *Pesticide Science* 51, 131-152) can be used for the determination of this property.

Possible penetration enhancers are for example alkanol alkoxylates. Penetration enhancers according to the invention are alkanol alkoxylates of the formula $$R\!-\!O\text{-}(\text{-}AO)_v\!-\!R'\quad (\text{III})$$

in which
R stands for linear or branched alkyl with 4 to 20 carbon atoms,
R' stands for hydrogen, methyl, ethyl, n-propyl, i-propyl, n-butyl, i-butyl, t-butyl, n-pentyl or n-hexyl,
AO stands for an ethylene oxide residue, a propylene oxide residue, a butylene oxide residue or for mixtures of ethylene oxide and propylene oxide residues or butylene oxide residues and
v stands for numbers from 2 to 30.

A preferred group of penetration enhancers are alkanol alkoxylates of the formula $$R\!-\!O\text{-}(\text{-}EO\!-\!)_n\!-\!R'\quad (\text{III-a})$$

in which
R has the aforesaid meaning,
R' has the aforesaid meaning,
EO stands for $-CH_2-C_2-O-$ and
n stands for numbers from 2 to 20.

A further preferred group of penetration enhancers are alkanol alkoxylates of the formula $$R\!-\!O\text{-}(\text{-}EO\!-\!)_p\!-\!(\!-\!PO\!-\!)_q\!-\!R'\quad (\text{III-b})$$

in which
R has the aforesaid meaning,
R' has the aforesaid meaning,
EO stands for $-CH_2-CH_2-O-$,
PO stands for $$-CH_2-\underset{\underset{CH_3}{|}}{CH}-O-,$$

p stands for numbers from 1 to 10 and
q stands for numbers from 1 to 10.

A further preferred group of penetration enhancers are alkanol alkoxylates of the formula $$R\!-\!O\!-\!(\!-\!PO\text{-}\!)_r\text{-}(EO\!-\!)_s\!-\!R'\quad (\text{III-c})$$

in which
R has the aforesaid meaning,
R' has the aforesaid meaning,
EO stands for $-CH_2-CH_2-O-$,
PO stands for $$-CH_2-\underset{\underset{CH_3}{|}}{CH}-O-,$$

r stands for numbers from 1 to 10 and
s stands for numbers from 1 to 10.

A further preferred group of penetration enhancers are alkanol alkoxylates of the formula $$R\!-\!O\text{-}(\text{-}EO\!-\!)_p\!-\!(\!-\!BO\!-\!)_q\!-\!R'\quad (\text{III-d})$$

in which
R and R' have the aforesaid meanings,
EO stands for $CH_2-CH_2-O-$,
BO stands for $$-CH_2-CH_2-\underset{\underset{CH_3}{|}}{CH}-O-,$$

p stands for numbers from 1 to 10 and
q stands for numbers from 1 to 10.

A further preferred group of penetration enhancers are alkanol alkoxylates of the formula $$R\!-\!O\!-\!(\!-\!BO\text{-}\!)_r\text{-}(\text{-}EO\!-\!)_s\!-\!R'\quad (\text{III-e})$$

in which
R and R' have the aforesaid meanings,
BO stands for $$-CH_2-CH_2-\underset{\underset{CH_3}{|}}{CH}-O-,$$

EO stands for $CH_2-CH_2-O-$,
r stands for numbers from 1 to 10 and
s stands for numbers from 1 to 10.

A further preferred group of penetration enhancers are alkanol alkoxylates of the formula $$CH_3\!-\!(CH_2)_t\!-\!CH_2\!-\!O\!-\!(\!-\!CH_2\!-\!CH_2\!-\!O\!-\!)_u\!-\!R'\quad (\text{III-f})$$

in which
R' has the aforesaid meaning,
t stands for numbers from 8 to 13 and
u stands for numbers from 6 to 17.

In the aforesaid formulae
R preferably stands for butyl, i-butyl, n-pentyl, i-pentyl, neopentyl, n-hexyl, i-hexyl, n-octyl, i-octyl, 2-ethylhexyl, nonyl, i-nonyl, decyl, n-dodecyl, i-dodecyl, lauryl, myristyl, i-tridecyl, trimethyl-nonyl, palmityl, stearyl or eicosyl.

As an example of an alkanol alkoxylate of the formula (III-c), 2-ethylhexyl alkoxylate of the formula $$CH_3\!-\!CH_2\!-\!CH_2\!-\!CH_2\!-\!\underset{\underset{C_2H_5}{|}}{CH}\!-\!CH_2\!-\!O\!-\!(PO)_8\!-\!(EO)_6\!-\!H\quad (\text{III-c-1})$$

in which
EO stands for $-CH_2-CH_2-O-$,
PO stands for $$-CH_2-\underset{\underset{CH_3}{|}}{CH}-O-$$

and
the numbers 8 and 6 are average values may be mentioned.

As an example of an alkanol alkoxylate of the formula (III-d), the formula $$CH_3\!-\!(CH_2)_{10}\!-\!O\text{-}(\text{-}EO\!-\!)_6\!-\!(\!-\!BO\!-\!)_2\!-\!CH_3\quad (\text{III-d-1})$$

in which
BO stands for $CH_2$—$CH_2$—O—,
BO stands for

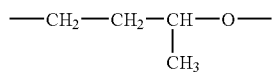

and
the numbers 10, 6 and 2 are average values, may be mentioned.

Particularly preferable alkanol alkoxylates of the formula (III-f) are compounds of this formula, in which
t stands for numbers from 9 to 12 and
u for numbers from 7 to 9.

Quite especially preferably, alkanol alkoxylate of the formula (III-f-1)

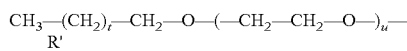

in which
t stands for the average value 10.5 and
u stands for the average value 8.4 may be mentioned.

The alkanol alkoxylates are generally defined by the above formulae. These substances are mixtures of substances of the stated type with different chain lengths. Average values, which can also deviate from whole numbers, are therefore calculated for the indices.

The alkanol alkoxylates of the stated formulae are known and some are commercially available or can be produced by known methods (see. WO 98/35 553, WO 00/35 278 and EP-A 0 681 865).

Also possible as penetration enhancers are for example substances which promote the solubility of the compounds of the formula (I) in the spray deposit. These for example include mineral or vegetable oils. Possible oils are all mineral or vegetable—optionally modified—oils normally usable in agrochemical agents. By way of example, sunflower oil, rape oil, olive oil, castor oil, turnip oil, corn seed oil, cottonseed oil and soybean oil or the esters of said oils may be mentioned. Rape oil, sunflower oil and the methyl or ethyl esters thereof are preferred.

The concentration of penetration enhancers in the agents according to the invention can be varied over a wide range. In a formulated pesticide, it is generally about 1 to 95 wt. %, preferably about 1 to 55 wt. %, particularly preferably about 15-40 wt. %. In the ready-to-use agents (sprays), the concentrations generally lie between 0.1 and 10 g/l, preferably between 0.5 and 5 g/l.

Combinations of active substance, salt and penetration enhancer emphasized according to the invention are set out in the following table. Here "as per test" means that any compound which acts as a penetration enhancer in the test for cuticle penetration (Baur et al., 1997, *Pesticide Science* 51, 131-152) is suitable.

TABLE 1

| No. | Active substance | Salt | Penetration enhancer |
|---|---|---|---|
| 1 | I, IA, IB | Ammonium sulfate | as per test |
| 2 | I, IA, IB | Ammonium lactate | as per test |
| 3 | I, IA, IB | Ammonium nitrate | as per test |
| 4 | I, IA, IB | Ammonium thiosulfate | as per test |
| 5 | I, IA, IB | Ammonium thiocyanate | as per test |
| 6 | I, IA, IB | Ammonium citrate | as per test |

TABLE 1-continued

| No. | Active substance | Salt | Penetration enhancer |
|---|---|---|---|
| 7 | I, IA, IB | Ammonium oxalate | as per test |
| 8 | I, IA, IB | Ammonium formate | as per test |
| 9 | I, IA, IB | Ammonium hydrogen phosphate | as per test |
| 10 | I, IA, IB | Ammonium dihydrogen phosphate | as per test |
| 11 | I, IA, IB | Ammonium carbonate | as per test |
| 12 | I, IA, IB | Ammonium benzoate | as per test |
| 13 | I, IA, IB | Ammonium sulfite | as per test |
| 14 | I, IA, IB | Ammonium benzoate | as per test |
| 15 | I, IA, IB | Ammonium hydrogen oxalate | as per test |
| 16 | I, IA, IB | Ammonium hydrogen citrate | as per test |
| 17 | I, IA, IB | Ammonium acetate | as per test |
| 18 | I, IA, IB | Tetramethylammonium sulfate | as per test |
| 19 | I, IA, IB | Tetramethylammonium lactate | as per test |
| 20 | I, IA, IB | Tetramethylammonium nitrate | as per test |
| 21 | I, IA, IB | Tetramethylammonium thiosulfate | as per test |
| 22 | I, IA, IB | Tetramethylammonium thiocyanate | as per test |
| 23 | I, IA, IB | Tetramethylammonium citrate | as per test |
| 24 | I, IA, IB | Tetramethylammonium oxalate | as per test |
| 25 | I, IA, IB | Tetramethylammonium formate | as per test |
| 26 | I, IA, IB | Tetramethylammonium hydrogen phosphate | as per test |
| 27 | I, IA, IB | Tetramethylammonium dihydrogen phosphate | as per test |
| 28 | I, IA, IB | Tetraethylammonium sulfate | as per test |
| 29 | I, IA, IB | Tetraethylammonium lactate | as per test |
| 30 | I, IA, IB | Tetraethylammonium nitrate | as per test |
| 31 | I, IA, IB | Tetraethylammonium thiosulfate | as per test |
| 32 | I, IA, IB | Tetraethylammonium thiocyanate | as per test |
| 33 | I, IA, IB | Tetraethylammonium citrate | as per test |
| 34 | I, IA, IB | Tetraethylammonium oxalate | as per test |
| 35 | I, IA, IB | Tetraethylammonium formate | as per test |
| 36 | I, IA, IB | Tetraethylammonium hydrogen phosphate | as per test |
| 37 | I, IA, IB | Tetraethylammonium dihydrogen phosphate | as per test |

Pesticides according to the invention can also contain other components, for example surfactants or dispersion aids or emulsifiers.

As nonionic surfactants or dispersion aids, all substances of this type normally usable in agro-chemical agents are possible. Preferably, polyethylene oxide polypropylene oxide block copolymers, polyethylene glycol ethers of linear alcohols, reaction products of fatty acids with ethylene oxide and/or propylene oxide, and also polyvinyl alcohol, polyvinylpyrrolidone, mixed polymerization products from polyvinyl alcohol and polyvinylpyrrolidone and copolymers of (meth)acrylic acid and (meth)acrylate esters, and also alkyl ethoxylates and alkylaryl ethoxylates, which can optionally be phosphated and optionally be neutralized with bases, may be mentioned, sorbitol ethoxylates being mentioned by way of example, and polyoxyalkylenamine derivatives.

As anionic surfactants, all substances of this type normally usable in agrochemical agents are possible. Alkali metal and alkaline earth metal salts of alkylsulfonic acids or alkylarylsulfonic acids are preferred.

A further preferred group of anionic surfactants or dispersion aids are poorly soluble in plant oil salts of polystyrenesulfonic acids, salts of polyvinylsulfonic acids, salts of naphthalenesulfonic acid-formaldehyde condensation products, salts of condensation products from naphthalenesulfonic acid, phenolsulfonic acid and formaldehyde and salts of ligninsulfonic acid.

Possible additives which can be contained in the formulations according to the invention are emulsifiers, foam suppressants, preservatives, antioxidants, colorants and inert fillers.

Preferred emulsifiers are ethoxylated alkylphenols, reaction products of alkylphenols with ethylene oxide and/or propylene oxide, ethoxylated arylalkylphenols, and also ethoxylated and propoxylated arylalkylphenols, and sulfated or phosphated arylalkyl ethoxylates or ethoxy-propoxylates, and sorbitan derivatives such as polyethylene oxide-sorbitan fatty acid esters and sorbitan fatty acid esters may be mentioned by way of example.

The following examples serve to illustrate the invention and should in no way be interpreted as limiting.

The compounds of the general formula (I) and (I-A) can have one or more chiral centers in the substituents A, $R^1$ to $R^5$, and are then present as mixtures of enantiomers or diastereomers. The present invention provides both the pure enantiomers or diastereomers and also mixtures thereof.

Salts of the compounds of the formula (I), (I-A) or (I-B) which are suitable for the use according to the invention are in particular agriculturally acceptable salts. These can be formed in standard ways, e.g. by reacting the compound with an acid of the anion in question.

Suitable agriculturally useful salts are in particular the salts of those cations or the acid addition salts of those acids, the cations or anions whereof have no adverse effects on the action of the compounds according to the invention which are suitable for the control of noxious insects or arachnids. Suitable cations are thus in particular the ions of the alkali metals, preferably lithium, sodium and potassium, the alkaline earth metals, preferably calcium, magnesium and barium, and the transition metals, preferably manganese, copper, zinc and iron, and the ammonium ion, which can if desired bear one to four $C_1$-$C_4$ alkyl substituents and/or a phenyl or benzyl substituent, preferably diisopropylammonium, tetramethylammonium, tetrabutylammonium or trimethyl-benzylammonium, or also phosphonium ions, sulfonium ions, preferably tri($C_1$-$C_4$ alkyl)sulfonium and sulfoxonium ions, preferably tri($C_1$-$C_4$ alkyl)sulfoxonium.

Anions of useful acid addition salts are first and foremost chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate and the anions of the $C_1$-$C_4$ alkanoic acids, preferably formate, acetate, propionate and butyrate. These can be formed by reacting the compounds of the formulae Ia and Ib with an acid of the corresponding anion, preferably hydrochloric acid, hydrobromic acid, sulfuric acid, phosphoric acid or nitric acid.

The organic residues mentioned in the aforesaid definitions of the variables, like the term halogen, are collective terms for particular enumerations of particular group members. The prefix "$C_n$-$C_m$" in each states the possible number of carbon atoms in the group.

In each case, the term halogen means fluorine, bromine, chlorine or iodine.

Examples of further meanings are:

In the present connection, the term "$C_1$-$C_4$ alkyl" and the alkyl residues of alkylamino and dialkylamino mean a saturated linear or branched hydrocarbon residue with 1 to 4 carbon atoms, i.e. for example methyl, ethyl, propyl, 1-methylethyl, butyl, 1-methylpropyl, 2-methylpropyl or 1,1-dimethylethyl.

In the present connection, the term "$C_1$-$C_6$ alkyl" means a saturated linear or branched hydrocarbon residue with 1 to 6 carbon atoms, i.e. for example one of the residues which were mentioned under $C_1$-$C_4$ alkyl, and n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

In the present connection, the term "$C_1$-$C_4$ haloalkyl" means a linear or saturated alkyl residue with 1 to 4 carbon atoms (as aforesaid), wherein some or all of the hydrogen atoms in these residues can be replaced by fluorine, chorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlordifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

In the present connection, the term "$C_1$-$C_2$ fluoroalkyl" means a $C_1$-$C_2$ alkyl residue which bears 1, 2, 3, 4 or 5 fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

In the present connection, the term "$C_1$-$C_4$ alkoxy" means a linear or branched saturated alkyl residue with 1 to 4 carbon atoms (as aforesaid), which is linked via an oxygen atom, i.e. for example methoxy, ethoxy, n-propoxy, 1-methylethoxy, n-butoxy, 1-methylpropoxy, 2-methylpropoxy or 1,1-dimethylethoxy.

In the present connection, the term "$C_1$-$C_4$ haloalkoxy" means a $C_1$-$C_4$ alkoxy residue as aforesaid, which is partly or wholly substituted with fluorine, chlorine, bromine and/or iodine, i.e. for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromo-propoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy.

In the present connection, the term "$C_1$-$C_4$ alkylthio($C_1$-$C_4$ alkylsulfanyl: $C_1$-$C_4$ alkyl-S—)" means a linear or branched saturated alkyl residue with 1 to 4 carbon atoms (as aforesaid), which is linked via a sulfur atom, i.e. for example methylthio, ethylthio, n-propylthio, 1-methylethylthio, butylthio, 1-methylpropylthio, 2-methylpropylthio or 1,1-dimethylethylthio.

In the present connection, the term "$C_1$-$C_4$ alkylsulfinyl" ($C_1$-$C_4$ alkyl-S(=O)—) means a linear or branched saturated hydrocarbon residue with 1 to 4 carbon atoms (as aforesaid), which is linked via the sulfur atom of the sulfinyl group to any bond in the alkyl residue, i.e. for example SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethyl]ethylsulfinyl, n-pentylsulfinyl, 1-methylbutylsulfinyl, 2-methylbutylsulfinyl, 3-methylbutylsulfinyl, 1,1- dimethylpropylsulfinyl, 1,2-dimethylpropylsulfinyl, 2,2-dimethylpropylsulfinyl or 1-ethylpropylsulfinyl.

In the present connection, the term "$C_1$-$C_4$ alkylsulfonyl" ($C_1$-$C_4$ alkyl-S(=O)$_2$—) means a linear or branched saturated alkyl residue with 1 to 4 carbon atoms (as aforesaid), which is linked via the sulfur atom of the sulfonyl group to any bond in the alkyl residue, i.e. for example SO$_2$—CH$_3$, SO$_2$—C$_2$H$_5$, n-propylsulfonyl, SO$_2$—CH(CH$_3$)$_2$, n-butylsulfonyl, 1-methylpropylsulfonyl, 2-methylpropylsulfonyl or SO$_2$—C(CH$_3$)$_3$.

In the present connection, the term "$C_1$-$C_4$ haloalkylthio" means a $C_1$-$C_4$ alkylthio residue as aforesaid, which is partly or wholly substituted with fluorine, chlorine, bromine and/or iodine, i.e. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio.

In the present connection, the term "$C_1$-$C_4$ alkoxycarbonyl" means a linear or branched saturated alkoxy residue with 1 to 4 carbon atoms (as aforesaid), which is linked via the carbon atom of the carbonyl group, i.e. for example methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl.

In the present connection, the term "$C_1$-$C_4$ alkylcarbonyl" means a linear or branched saturated alkyl residue with 1 to 4 carbon atoms (as aforesaid), which is linked via the carbon atom of the carbonyl group, i.e. for example methylcarbonyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl.

In the present connection, the term "($C_1$-$C_4$ alkylamino) carbonyl" for example means methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl.

In the present connection, the term "Di-($C_1$-$C_4$ alkyl)aminocarbonyl" for example means N,N-dimethylaminocarbonyl, N,N-diethylaminocarbonyl, N,N-di-(1-methylethyl)aminocarbonyl, N,N-dipropylaminocarbonyl, N,N-butylaminocarbonyl, N,N-di-(1-methylpropyl)aminocarbonyl, N,N-di(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl) aminocarbonyl, N-ethyl-N-(1,1-dimethylethyl) aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-methyl-ethyl)-N-(1-methylpropyl)aminocarbonyl, N-(1-methylethyl)-N-(2-methylpropyl)aminocarbonyl, N-(1,1-dimethylethyl)-N-(1-methylethyl)-aminocarbonyl, N-butyl-N-(1-methylpropyl)aminocarbonyl, N-butyl-N-(2-methylpropyl) amino-carbonyl, N-butyl-N-(1,1-dimethylethyl) aminocarbonyl, N-(1-methylpropyl)-N-(2-methylpropyl)-aminocarbonyl, N-(1,1-dimethylethyl)-N-(1-methylpropyl) aminocarbonyl or N-(1,1-dimethylethyl)-N-(2-methylpropyl)aminocarbonyl.

In the present connection, the term "$C_2$-$C_6$ alkenyl" means a linear or branched singly unsaturated hydrocarbon residue with 2 to 6 carbon atoms and a double bond in any position, i.e. for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

In the present connection, the term "$C_2$-$C_6$ alkynyl" means a linear or branched aliphatic hydrocarbon residue which contains a C—C triple bond and has 2 to 6 carbon atoms: for example ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

In the present connection, the term "$C_3$-$C_8$ cycloalkyl" means a mononuclear hydrocarbon residue with 3 to 8 carbon atoms, for example cyclopropyl, cyclobutyl, cyclopentyl, cyclohexyl, cycloheptyl or cyclooctyl.

Among the 2-cyanobenzenesulfonamide compounds of the general formula (I), (I-A) and (I-B), those are preferred wherein the variables A, $R^1$ and $R^2$ mutually independently, but in particular in combination, have the meanings set out below:

A means hydrogen, $C_1$-$C_4$ alkyl, in particular methyl or ethyl
$R^1$ means hydrogen, fluorine, chlorine, bromine, $C_1$-$C_2$ alkyl, in particular methyl, trifluoromethyl or $C_1$-$C_2$ alkoxy, in particular methoxy;
$R^2$ means hydrogen or a linear, cyclic or branched chain hydrocarbon residue with 1 to 4 carbon atoms, e.g. $C_1$-$C_4$ alkyl, in particular methyl, ethyl, n-propyl, 1-methylethyl, cyclopropyl, $C_1$-$C_4$ alkoxy-$C_1$-$C_4$ alkyl, in particular 2-methoxyethyl, $C_1$-$C_4$ alkylthio-$C_1$-$C_4$ alkyl, in particular 2-methylthioethyl or $C_2$-$C_4$ alkynyl, in particular prop-2-yn-1-yl (propargyl). Most strongly preferred are compounds I in which A stands for hydrogen and $R^2$ is from the range methyl, ethyl, 1-methylethyl and prop-2-yn-1-yl.

Also preferred are those 2-cyanobenzenesulfonamide compounds of the general formula (I), (I-A) and (I-B) in which $R^1$ means $C_1$-$C_4$ haloalkoxy, especially $C_1$ haloalkoxy, in particular trifluoromethoxy, difluoromethoxy or chlorodifluoromethoxy. In these compounds, A has the aforesaid meanings, preferably hydrogen, methyl or ethyl and $R^2$ the aforesaid meanings, preferably hydrogen or a linear, cyclic or branched chain hydrocarbon residue with 1 to 4 carbon atoms, e.g. $C_1$-$C_4$ alkyl, especially methyl, ethyl, n-propyl, 1-methylethyl, cyclopropyl, $C_1$-$C_4$ alkoxy-$C_1$-$C_4$ alkyl, especially 2-methoxyethyl, $C_1$-$C_4$ alkylthio-$C_1$-$C_4$ alkyl, especially 2-methylthioethyl or $C_2$-$C_4$ alkynyl, especially prop-2-yn-1-yl (propargyl). Most strongly preferred are compounds of the formula (I) and (I-A), in which A for hydrogen and $R^2$ is from the range methyl, ethyl, 1-methylethyl and prop-2-yn-1-yl.

A preferred embodiment of the present invention relates to 2-cyanobenzenesulfonamide compounds of the general formula (I), (I-A) and (I-B) in which the variables A, $R^1$ and $R^2$ have the aforesaid meanings, in particular those meanings which are cited as preferred, and at least one of the residues $R^3$, $R^4$ or $R^5$ differs from hydrogen, and preferably one or two of the residues $R^3$, $R^4$ or $R^5$ mean hydrogen. Among these compounds, those compounds are preferred in which $R^3$ differs from hydrogen and preferably means halogen, in particular chlorine or fluorine, and the other residues $R^4$ and $R^5$ mean hydrogen.

A further preferred embodiment of the present invention relates to 2-cyanobenzenesulfonamide compounds of the general formula (I), (I-A) and (I-B), in which the variables A, $R^1$ and $R^2$ have the aforesaid meanings, in particular those meanings which are cited as preferred, and each of the residues $R^3$, $R^4$ and $R^5$ means hydrogen.

Examples of preferred compounds according to the invention of the formula (I),

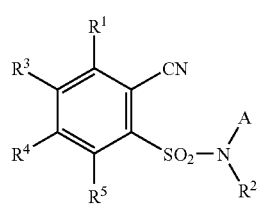

(I)

which can optionally be present in their isomeric formulae (I-A) and (I-B), include those compounds which are cited in the following tables A1 to A16, wherein A, $R^3$, $R^4$, $R^5$ are as defined in the tables, and $R^1$ and $R^2$ are cited in the rows of table A:

Table A1: compounds of the formula I wherein each of the residues A, $R^3$, $R^4$ and $R^5$ means hydrogen and $R^1$ and $R^2$ are as defined in a row in table A.
Table A2: compounds of the formula I wherein $R^3$ means chlorine, A, $R^4$ and $R^5$ mean hydrogen and $R^1$ and $R^2$ are as defined in a row in table A.
Table A3: compounds of the formula I wherein $R^3$ means fluorine, A, $R^4$ and $R^5$ mean hydrogen and $R^1$ and $R^2$ are as defined in a row in table A.
Table A4: compounds of the formula I wherein $R^3$ means bromine, A, $R^4$ and $R^5$ mean hydrogen and $R^1$ and $R^2$ are as defined in a row in table A.
Table A5: compounds of the formula I wherein $R^3$ means iodine, A, $R^4$ and $R^5$ mean hydrogen and $R^1$ and $R^2$ are as defined in a row in table A.
Table A6: compounds of the formula I wherein $R^3$ means $CH_3$, A, $R^4$ and $R^5$ mean hydrogen and $R^1$ and $R^2$ are as defined in a row in table A.
Table A7: compounds of the formula I wherein $R^4$ means chlorine, A, $R^3$ and $R^5$ mean hydrogen and $R^1$ and $R^2$ are as defined in a row in table A.
Table A8: compounds of the formula I wherein $R^4$ means fluorine, A, $R^3$ and $R^5$ mean hydrogen and $R^1$ and $R^2$ are as defined in a row in table A.
Table A9: compounds of the formula I wherein $R^4$ means bromine, A, $R^3$ and $R^5$ mean hydrogen and $R^1$ and $R^2$ are as defined in a row in table A.
Table A10: compounds of the formula I wherein $R^4$ means iodine, A, $R^3$ and $R^5$ mean hydrogen and $R^1$ and $R^2$ are as defined in a row in table A.
Table A11: compounds of the formula I wherein $R^4$ means $CH_3$, A, $R^3$ and $R^5$ mean hydrogen and $R^1$ and $R^2$ are as defined in a row in table A.
Table A12: compounds of the formula I wherein $R^5$ means chlorine, A, $R^3$ and $R^4$ mean hydrogen and $R^1$ and $R^2$ are as defined in a row in table A.
Table A13: compounds of the formula I wherein $R^5$ means fluorine, A, $R^3$ and $R^4$ mean hydrogen and $R^1$ and $R^2$ are as defined in a row in table A.
Table A14: compounds of the formula I wherein $R^5$ means bromine, A, $R^3$ and $R^4$ mean hydrogen and $R^1$ and $R^2$ are as defined in a row in table A.
Table A15: compounds of the formula I wherein $R^5$ means iodine, A, $R^3$ and $R^4$ mean hydrogen and $R^1$ and $R^2$ are as defined in a row in table A.
Table A16: compounds of the formula I wherein $R^5$ means $CH_3$, A, $R^3$ and $R^4$ mean hydrogen and $R^1$ and $R^2$ are as defined in a row in table A.

TABLE A

| | $R^1$ | $R^2$ |
|---|---|---|
| 1. | $CH_3$ | H |
| 2. | $CH_3$ | $CH_3$ |
| 3. | $CH_3$ | $CH_3CH_2$— |
| 4. | $CH_3$ | $(CH_3)_2CH$— |
| 5. | $CH_3$ | $CH_3CH_2CH_2$— |
| 6. | $CH_3$ | n-$C_4H_9$ |
| 7. | $CH_3$ | $(CH_3)_3C$— |
| 8. | $CH_3$ | $(CH_3)_2CHCH_2$— |
| 9. | $CH_3$ | n-$C_5H_{11}$ |
| 10. | $CH_3$ | $(CH_3)_2CH$—$CH_2$—$CH_2$— |
| 11. | $CH_3$ | $(C_2H_5)_2$—CH— |
| 12. | $CH_3$ | $(CH_3)_3C$—$CH_2$— |
| 13. | $CH_3$ | $(CH_3)_3C$—$CH_2$—$CH_2$— |
| 14. | $CH_3$ | $C_2H_5CH(CH_3)$—$CH_2$— |
| 15. | $CH_3$ | $CH_3$—$CH_2$—$C(CH_3)_2$— |
| 16. | $CH_3$ | $(CH_3)_2CH$—$CH(CH_3)$— |
| 17. | $CH_3$ | $(CH_3)_3C$—$CH(CH_3)$— |

TABLE A-continued

| | R$^1$ | R$^2$ |
|---|---|---|
| 18. | CH$_3$ | (CH$_3$)$_2$CH—CH$_2$—CH(CH$_3$)— |
| 19. | CH$_3$ | CH$_3$—CH$_2$—C(CH$_3$)(C$_2$H$_5$)— |
| 20. | CH$_3$ | CH$_3$—CH$_2$—CH$_2$—C(CH$_3$)$_2$— |
| 21. | CH$_3$ | C$_2$H$_5$—CH$_2$—CH(CH$_3$)—CH$_2$— |
| 22. | CH$_3$ | cyclopropyl |
| 23. | CH$_3$ | cyclopropyl-CH$_2$— |
| 24. | CH$_3$ | cyclopropyl-CH(CH$_3$)— |
| 25. | CH$_3$ | cyclobutyl |
| 26. | CH$_3$ | cyclopentyl |
| 27. | CH$_3$ | cyclohexyl |
| 28. | CH$_3$ | HC≡C—CH$_2$— |
| 29. | CH$_3$ | HC≡C—CH(CH$_3$)— |
| 30. | CH$_3$ | HC≡C—C(CH$_3$)$_2$— |
| 31. | CH$_3$ | HC≡C—C(CH$_3$)(C$_2$H$_5$)— |
| 32. | CH$_3$ | HC≡C—C(CH$_3$)(C$_3$H$_7$)— |
| 33. | CH$_3$ | CH$_2$=CH—CH$_2$— |
| 34. | CH$_3$ | H$_2$C=CH—CH(CH$_3$)— |
| 35. | CH$_3$ | H$_2$C=CH—C(CH$_3$)$_2$— |
| 36. | CH$_3$ | H$_2$C=CH—C(C$_2$H$_5$)(CH$_3$)— |
| 37. | CH$_3$ | C$_6$H$_5$—CH$_2$— |
| 38. | CH$_3$ | 4-(CH$_3$)$_3$C—C$_6$H$_4$—CH$_2$— |
| 39. | CH$_3$ | C$_6$H$_5$—CH$_2$— |
| 40. | CH$_3$ | 4-(CH$_3$)$_3$C—C$_6$H$_4$—CH$_2$— |
| 41. | CH$_3$ | 4-Cl—C$_6$H$_4$—CH$_2$— |
| 42. | CH$_3$ | 3-(CH$_3$O)—C$_6$H$_4$—CH$_2$— |
| 43. | CH$_3$ | 4-(CH$_3$O)—C$_6$H$_4$—CH$_2$— |
| 44. | CH$_3$ | 2-(CH$_3$O)—C$_6$H$_4$—CH$_2$— |
| 45. | CH$_3$ | 3-Cl—C$_6$H$_4$—CH$_2$— |
| 46. | CH$_3$ | 2-Cl—C$_6$H$_4$—CH$_2$— |
| 47. | CH$_3$ | 4-(F$_3$C)—C$_6$H$_4$—CH$_2$— |
| 48. | CH$_3$ | NC—CH$_2$— |
| 49. | CH$_3$ | NC—CH$_2$—CH$_2$— |
| 50. | CH$_3$ | NC—CH$_2$CH(CH$_3$)— |
| 51. | CH$_3$ | NC—CH$_2$C(CH$_3$)$_2$— |
| 52. | CH$_3$ | NC—CH$_2$—CH$_2$—CH$_2$— |
| 53. | CH$_3$ | FH$_2$C—CH$_2$— |
| 54. | CH$_3$ | ClH$_2$C—CH$_2$— |
| 55. | CH$_3$ | BrH$_2$C—CH$_2$— |
| 56. | CH$_3$ | FH$_2$C—CH(CH$_3$)— |
| 57. | CH$_3$ | ClH$_2$C—CH(CH$_3$)— |
| 58. | CH$_3$ | BrH$_2$C—CH(CH$_3$)— |
| 59. | CH$_3$ | F$_2$HC—CH$_2$— |
| 60. | CH$_3$ | F$_3$C—CH$_2$— |
| 61. | CH$_3$ | FH$_2$C—CH$_2$—CH$_2$— |
| 62. | CH$_3$ | ClH$_2$C—CH$_2$—CH$_2$— |
| 63. | CH$_3$ | BrH$_2$C—CH$_2$—CH$_2$— |
| 64. | CH$_3$ | F$_2$HC—CH$_2$—CH$_2$— |
| 65. | CH$_3$ | F$_3$C—CH$_2$—CH$_2$— |
| 66. | CH$_3$ | CH$_3$—O—CH$_2$—CH$_2$— |
| 67. | CH$_3$ | CH$_3$—S—CH$_2$—CH$_2$— |
| 68. | CH$_3$ | CH$_3$—SO$_2$—CH$_2$—CH$_2$— |
| 69. | CH$_3$ | C$_2$H$_5$—O—CH$_2$—CH$_2$— |
| 70. | CH$_3$ | (CH$_3$)$_2$CH—O—CH$_2$—CH$_2$— |
| 71. | CH$_3$ | C$_2$H$_5$—S—CH$_2$—CH$_2$— |
| 72. | CH$_3$ | C$_2$H$_5$—SO$_2$—CH$_2$—CH$_2$— |
| 73. | CH$_3$ | (CH$_3$)$_2$N—CH$_2$—CH$_2$— |
| 74. | CH$_3$ | (C$_2$H$_5$)$_2$N—CH$_2$—CH$_2$— |
| 75. | CH$_3$ | [(CH$_3$)$_2$CH]$_2$N—CH$_2$—CH$_2$— |
| 76. | CH$_3$ | CH$_3$—O—CH$_2$—CH(CH$_3$)— |
| 77. | CH$_3$ | CH$_3$—S—CH$_2$—CH(CH$_3$)— |
| 78. | CH$_3$ | CH$_3$—SO$_2$—CH$_2$—CH(CH$_3$)— |
| 79. | CH$_3$ | C$_2$H$_5$—O—CH$_2$—CH(CH$_3$)— |
| 80. | CH$_3$ | C$_2$H$_5$—S—CH$_2$—CH(CH$_3$)— |
| 81. | CH$_3$ | C$_2$H$_5$—SO$_2$—CH$_2$—CH(CH$_3$)— |
| 82. | CH$_3$ | (CH$_3$)$_2$N—CH$_2$—CH(CH$_3$)— |
| 83. | CH$_3$ | (C$_2$H$_5$)$_2$N—CH$_2$—CH{CH$_3$}— |
| 84. | CH$_3$ | [(CH$_3$)$_2$CH]$_2$N—CH$_2$—CH(CH$_3$)— |
| 85. | CH$_3$ | CH$_3$—O—CH(CH$_3$)—CH$_2$— |
| 86. | CH$_3$ | CH$_3$—S—CH(CH$_3$)—CH$_2$— |
| 87. | CH$_3$ | CH$_3$—SO$_2$—CH(CH$_3$)—CH$_2$— |
| 88. | CH$_3$ | C$_2$H$_5$—O—CH(CH$_3$)—CH$_2$— |
| 89. | CH$_3$ | C$_2$H$_5$—S—CH(CH$_3$)—CH$_2$— |
| 90. | CH$_3$ | C$_2$H$_5$—SO$_2$—CH(CH$_3$)—CH$_2$— |
| 91. | CH$_3$ | (CH$_3$)$_2$N—CH(CH$_3$)—CH$_2$— |
| 92. | CH$_3$ | (C$_2$H$_5$)$_2$N—CH(CH$_3$)—CH$_2$— |
| 93. | CH$_3$ | [(CH$_3$)$_2$CH]$_2$N—CH(CH$_3$)—CH$_2$— |
| 94. | CH$_3$ | CH$_3$—O—CH$_2$—CH$_2$—CH$_2$— |
| 95. | CH$_3$ | CH$_3$—S—CH$_2$—CH$_2$—CH$_2$— |
| 96. | CH$_3$ | CH$_3$—SO$_2$—CH$_2$—CH$_2$—CH$_2$— |
| 97. | CH$_3$ | C$_2$H$_5$—O—CH$_2$—CH$_2$—CH$_2$— |
| 98. | CH$_3$ | C$_2$H$_5$—S—CH$_2$—CH$_2$—CH$_2$— |
| 99. | CH$_3$ | C$_2$H$_5$—SO$_2$—CH$_2$—CH$_2$—CH$_2$— |
| 100. | CH$_3$ | (CH$_3$)$_2$N—CH$_2$—CH$_2$CH$_2$— |
| 101. | CH$_3$ | (C$_2$H$_5$)$_2$N—CH$_2$—CH$_2$—CH$_2$— |
| 102. | CH$_3$ | CH$_3$—O—CH$_2$—C(CH$_3$)$_2$— |
| 103. | CH$_3$ | CH$_3$—S—CH$_2$—C(CH$_3$)$_2$— |
| 104. | CH$_3$ | CH$_3$—SO$_2$—CH$_2$—C(CH$_3$)$_2$— |
| 105. | CH$_3$ | C$_2$H$_5$—O—CH$_2$—C(CH$_3$)$_2$— |
| 106. | CH$_3$ | C$_2$H$_5$—S—CH$_2$—C(CH$_3$)$_2$— |
| 107. | CH$_3$ | C$_2$H$_5$—SO$_2$—CH$_2$—C(CH$_3$)$_2$— |
| 108. | CH$_3$ | (CH$_3$)$_2$N—CH$_2$—C(CH$_3$)$_2$— |
| 109. | CH$_3$ | (C$_2$H$_5$)$_2$N—CH$_2$—C(CH$_3$)$_2$— |
| 110. | CH$_3$ | [(CH$_3$)$_2$CH]$_2$N—CH$_2$—C(CH$_3$)$_2$— |
| 111. | CH$_3$ | Cl—CH$_2$—C≡C—CH$_2$— |
| 112. | CH$_3$ | CH$_3$—O—C(O)—CH$_2$— |
| 113. | CH$_3$ | C$_2$H$_5$—O—C(O)—CH$_2$— |
| 114. | CH$_3$ | CH$_3$—O—C(O)—CH(CH$_3$)— |
| 115. | CH$_3$ | C$_2$H$_5$—O—C(O)—CH(CH$_3$)— |
| 116. | CH$_3$ | (CH$_3$O)$_2$CH—CH$_2$— |
| 117. | CH$_3$ | (C$_2$H$_5$O)$_2$—CH—CH$_2$— |
| 118. | C$_2$H$_5$ | H |
| 119. | C$_2$H$_5$ | CH$_3$ |
| 120. | C$_2$H$_5$ | CH$_3$CH$_2$— |
| 121. | C$_2$H$_5$ | (CH$_3$)$_2$CH— |
| 122. | C$_2$H$_5$ | CH$_3$CH$_2$CH$_2$— |
| 123. | C$_2$H$_5$ | n-C$_4$H$_9$ |
| 124. | C$_2$H$_5$ | (CH$_3$)$_3$C— |
| 125. | C$_2$H$_5$ | (CH$_3$)$_2$CH—CH$_2$— |
| 126. | C$_2$H$_5$ | n-C$_5$H$_{11}$ |
| 127. | C$_2$H$_5$ | (CH$_3$)$_2$CH—CH$_2$CH$_2$— |
| 128. | C$_2$H$_5$ | (C$_2$H$_5$)$_2$—CH— |
| 129. | C$_2$H$_5$ | (CH$_3$)$_3$C—CH$_2$— |
| 130. | C$_2$H$_5$ | (CH$_3$)$_3$C—CH$_2$—CH$_2$— |
| 131. | C$_2$H$_5$ | C$_2$H$_5$—CH$_2$—CH(CH$_3$)— |
| 132. | C$_2$H$_5$ | CH$_3$—CH$_2$—C(CH$_3$)$_2$— |
| 133. | C$_2$H$_5$ | (CH$_3$)$_2$CH—CH(CH$_3$)— |
| 134. | C$_2$H$_5$ | (CH$_3$)$_3$C—CH(CH$_3$)— |
| 135. | C$_2$H$_5$ | (CH$_3$)$_2$CH—CH$_2$—CH(CH$_3$)— |
| 136. | C$_2$H$_5$ | CH$_3$—CH$_2$—C(CH$_3$)(C$_2$H$_5$)— |
| 137. | C$_2$H$_5$ | CH$_3$—CH$_2$—CH$_2$—C(CH$_3$)$_2$— |
| 138. | C$_2$H$_5$ | C$_2$H$_5$—CH$_2$—CH(CH$_3$)—CH$_2$— |
| 139. | C$_2$H$_5$ | cyclopropyl |
| 140. | C$_2$H$_5$ | cyclopropyl-CH$_2$— |
| 141. | C$_2$H$_5$ | cyclopropyl-CH(CH$_3$)— |
| 142. | C$_2$H$_5$ | cyclobutyl |
| 143. | C$_2$H$_5$ | cyclopentyl |
| 144. | C$_2$H$_5$ | cyclohexyl |
| 145. | C$_2$H$_5$ | HC≡C—CH$_2$— |
| 146. | C$_2$H$_5$ | HC≡C—CH(CH$_3$)— |
| 147. | C$_2$H$_5$ | HC≡C—C(CH$_3$)$_2$— |
| 148. | C$_2$H$_5$ | HC≡C—C(CH$_3$)(C$_2$H$_5$)— |
| 149. | C$_2$H$_5$ | HC≡C—C(CH$_3$)(C$_3$H$_7$)— |
| 150. | C$_2$H$_5$ | CH$_2$=CH—CH$_2$— |
| 151. | C$_2$H$_5$ | H$_2$C=CH—CH(CH$_3$)— |
| 152. | C$_2$H$_5$ | H$_2$C=CH—C(CH$_3$)$_2$— |
| 153. | C$_2$H$_5$ | H$_2$C=CH—C(C$_2$H$_5$)(CH$_3$)— |
| 154. | C$_2$H$_5$ | C$_6$H$_5$—CH$_2$— |
| 155. | C$_2$H$_5$ | 4-(CH$_3$)$_3$C—C$_6$H$_4$—CH$_2$— |
| 156. | C$_2$H$_5$ | C$_6$H$_5$—CH$_2$— |
| 157. | C$_2$H$_5$ | 4-(CH$_3$)$_3$C—C$_6$H$_4$—CH$_2$— |
| 158. | C$_2$H$_5$ | 4-Cl—C$_6$H$_4$—CH$_2$— |
| 159. | C$_2$H$_5$ | 3-(CH$_3$O)—C$_6$H$_4$—CH$_2$— |
| 160. | C$_2$H$_5$ | 4-(CH$_3$O)—C$_6$H$_4$—CH$_2$— |
| 161. | C$_2$H$_5$ | 2-(CH$_3$O)—C$_6$H$_4$—CH$_2$— |
| 162. | C$_2$H$_5$ | 3-Cl—C$_6$H$_4$—CH$_2$— |
| 163. | C$_2$H$_5$ | 2-Cl—C$_6$H$_4$—CH$_2$— |
| 164. | C$_2$H$_5$ | 4-(F$_3$C)—C$_6$H$_4$—CH$_2$— |
| 165. | C$_2$H$_5$ | NC—CH$_2$— |
| 166. | C$_2$H$_5$ | NC—CH$_2$—CH$_2$— |
| 167. | C$_2$H$_5$ | NC—CH$_2$—CH(CH$_3$)— |
| 168. | C$_2$H$_5$ | NC—CH$_2$—C(CH$_3$)$_2$— |
| 169. | C$_2$H$_5$ | NC—CH$_2$—CH$_2$—CH$_2$— |
| 170. | C$_2$H$_5$ | FH$_2$C—CH$_2$— |
| 171. | C$_2$H$_5$ | ClH$_2$C—CH$_2$— |
| 172. | C$_2$H$_5$ | BrH$_2$C—CH$_2$— |
| 173. | C$_2$H$_5$ | FH$_2$C—CH(CH$_3$)— |

TABLE A-continued

| | R¹ | R² |
|---|---|---|
| 174. | $C_2H_5$ | $ClH_2C-CH(CH_3)-$ |
| 175. | $C_2H_5$ | $BrH_2C-CH(CH_3)-$ |
| 176. | $C_2H_5$ | $F_2HC-CH_2-$ |
| 177. | $C_2H_5$ | $F_3C-CH_2-$ |
| 178. | $C_2H_5$ | $FH_2C-CH_2-CH_2-$ |
| 179. | $C_2H_5$ | $ClH_2C-CH_2-CH_2-$ |
| 180. | $C_2H_5$ | $BrH_2C-CH_2-CH_2-$ |
| 181. | $C_2H_5$ | $F_2HC-CH_2-CH_2-$ |
| 182. | $C_2H_5$ | $F_3C-CH_2-CH_2-$ |
| 183. | $C_2H_5$ | $CH_3-O-CH_2-CH_2-$ |
| 184. | $C_2H_5$ | $CH_3-S-CH_2-CH_2-$ |
| 185. | $C_2H_5$ | $CH_3-SO_2-CH_2-CH_2-$ |
| 186. | $C_2H_5$ | $C_2H_5-O-CH_2-CH_2-$ |
| 187. | $C_2H_5$ | $(CH_3)_2CH-O-CH_2-CH_2-$ |
| 188. | $C_2H_5$ | $C_2H_5-S-CH_2-CH_2-$ |
| 189. | $C_2H_5$ | $C_2H_5-SO_2-CH_2-CH_2-$ |
| 190. | $C_2H_5$ | $(CH_3)_2N-CH_2-CH_2-$ |
| 191. | $C_2H_5$ | $(C_2H_5)_2N-CH_2-CH_2-$ |
| 192. | $C_2H_5$ | $[(CH_3)_2CH]_2N-CH_2-CH_2-$ |
| 193. | $C_2H_5$ | $CH_3-O-CH_2-CH(CH_3)-$ |
| 194. | $C_2H_5$ | $CH_3S-CH_2-CH(CH_3)-$ |
| 195. | $C_2H_5$ | $CH_3-SO_2-CH_2-CH(CH_3)-$ |
| 196. | $C_2H_5$ | $C_2H_5-O-CH_2-CH(CH_3)-$ |
| 197. | $C_2H_5$ | $C_2H_5-S-CH_2CH(CH_3)-$ |
| 198. | $C_2H_5$ | $C_2H_5-SO_2-CH_2-CH(CH_3)-$ |
| 199. | $C_2H_5$ | $(CH_3)_2N-CH_2-CH(CH_3)-$ |
| 200. | $C_2H_5$ | $(C_2H_5)_2N-CH_2-CH(CH_3)-$ |
| 201. | $C_2H_5$ | $[(CH_3)_2CH]_2N-CH_2-CH(CH_3)-$ |
| 202. | $C_2H_5$ | $CH_3-O-CH(CH_3)-CH_2-$ |
| 203. | $C_2H_5$ | $CH_3-S-CH(CH_3)-CH_2-$ |
| 204. | $C_2H_5$ | $CH_3-SO_2-CH(CH_3)-CH_2-$ |
| 205. | $C_2H_5$ | $C_2H_5-O-CH(CH_3)-CH_2-$ |
| 206. | $C_2H_5$ | $C_2H_5-S-CH(CH_3)-CH_2-$ |
| 207. | $C_2H_5$ | $C_2H_5-SO_2-CH(CH_3)-CH_2-$ |
| 208. | $C_2H_5$ | $(CH_3)_2N-CH(CH_3)-CH_2-$ |
| 209. | $C_2H_5$ | $(C_2H_5)_2N-CH(CH_3)-CH_2-$ |
| 210. | $C_2H_5$ | $[(CH_3)_2CH]_2N-CH(CH_3)-CH_2-$ |
| 211. | $C_2H_5$ | $CH_3-O-CH_2-CH_2-CH_2-$ |
| 212. | $C_2H_5$ | $CH_3-S-CH_2-CH_2-CH_2-$ |
| 213. | $C_2H_5$ | $CH_3-SO_2-CH_2-CH_2-CH_2-$ |
| 214. | $C_2H_5$ | $C_2H_5-O-CH_2-CH_2-CH_2-$ |
| 215. | $C_2H_5$ | $C_2H_5-S-CH_2-CH_2-CH_2-$ |
| 216. | $C_2H_5$ | $C_2H_5-SO_2-CH_2-CH_2-CH_2-$ |
| 217. | $C_2H_5$ | $(CH_3)_2N-CH_2-CH_2-CH_2-$ |
| 218. | $C_2H_5$ | $(C_2H_5)_2N-CH_2-CH_2-CH_2-$ |
| 219. | $C_2H_5$ | $CH_3-O-CH_2-C(CH_3)_2-$ |
| 220. | $C_2H_5$ | $CH_3-S-CH_2-C(CH_3)_2-$ |
| 221. | $C_2H_5$ | $CH_3-SO_2-CH_2-C(CH_3)_2-$ |
| 222. | $C_2H_5$ | $C_2H_5-O-CH_2-C(CH_3)_2-$ |
| 223. | $C_2H_5$ | $C_2H_5-S-CH_2-C(CH_3)_2-$ |
| 224. | $C_2H_5$ | $C_2H_5-SO_2-CH_2-C(CH_3)_2-$ |
| 225. | $C_2H_5$ | $(CH_3)_2N-CH_2-C(CH_3)_2-$ |
| 226. | $C_2H_5$ | $(C_2H_5)_2N-CH_2-C(CH_3)_2-$ |
| 227. | $C_2H_5$ | $[(CH_3)_2CH]_2N-CH_2-C(CH_3)_2-$ |
| 228. | $C_2H_5$ | $Cl-CH_2-C\equiv C-CH_2-$ |
| 229. | $C_2H_5$ | $CH_3-O-C(O)-CH_2$ |
| 230. | $C_2H_5$ | $C_2H_5-O-C(O)-CH_2$ |
| 231. | $C_2H_5$ | $CH_3-O-C(O)-CH(CH_3)-$ |
| 232. | $C_2H_5$ | $C_2H_5-O-C(O)-CH(CH_3)-$ |
| 233. | $C_2H_5$ | $(CH_3O)_2CH-CH_2-$ |
| 234. | $C_2H_5$ | $(C_2H_5O)_2CH-CH_2-$ |
| 235. | $OCH_3$ | H |
| 236. | $OCH_3$ | $CH_3$ |
| 237. | $OCH_3$ | $CH_3CH_2-$ |
| 238. | $OCH_3$ | $(CH_3)_2CH-$ |
| 239. | $OCH_3$ | $CH_3CH_2CH_2-$ |
| 240. | $OCH_3$ | $n-C_4H_9$ |
| 241. | $OCH_3$ | $(CH_3)_3C-$ |
| 242. | $OCH_3$ | $(CH_3)_2CH-CH_2-$ |
| 243. | $OCH_3$ | $n-C_5H_{11}$ |
| 244. | $OCH_3$ | $(CH_3)_2CH-CH_2-CH_2-$ |
| 245. | $OCH_3$ | $(C_2H_5)_2-CH-$ |
| 246. | $OCH_3$ | $(CH_3)_3C-CH_2-$ |
| 247. | $OCH_3$ | $(CH_3)_3C-CH_2-CH_2-$ |
| 248. | $OCH_3$ | $C_2H_5CH(CH_3)-CH_2-$ |
| 249. | $OCH_3$ | $CH_3-CH_2-C(CH_3)_2-$ |
| 250. | $OCH_3$ | $(CH_3)_2CH-CH(CH_3)-$ |
| 251. | $OCH_3$ | $(CH_3)_3C-CH(CH_3)-$ |
| 252. | $OCH_3$ | $(CH_3)_2CH-CH_2-CH(CH_3)-$ |
| 253. | $OCH_3$ | $CH_3-CH_2-C(CH_3)(C_2H_5)-$ |
| 254. | $OCH_3$ | $CH_3-CH_2-CH_2-C(CH_3)_2-$ |
| 255. | $OCH_3$ | $C_2H_5-CH_2-CH(CH_3)-CH_2-$ |
| 256. | $OCH_3$ | cyclopropyl |
| 257. | $OCH_3$ | cyclopropyl-$CH_2-$ |
| 258. | $OCH_3$ | cyclopropyl-$CH(CH_3)-$ |
| 259. | $OCH_3$ | cyclobutyl |
| 260. | $OCH_3$ | cyclopentyl |
| 261. | $OCH_3$ | cyclohexyl |
| 262. | $OCH_3$ | $HC\equiv C-CH_2-$ |
| 263. | $OCH_3$ | $HC\equiv C-CH(CH_3)-$ |
| 264. | $OCH_3$ | $HC\equiv C-C(CH_3)_2-$ |
| 265. | $OCH_3$ | $HC\equiv C-C(CH_3)(C_2H_5)-$ |
| 266. | $OCH_3$ | $HC\equiv C-C(CH_3)(C_3H_7)-$ |
| 267. | $OCH_3$ | $CH_2=CH-CH_2-$ |
| 268. | $OCH_3$ | $H_2C=CH-CH(CH_3)-$ |
| 269. | $OCH_3$ | $H_2C=CH-C(CH_3)_2-$ |
| 270. | $OCH_3$ | $H_2C=CH-C(C_2H_5)(CH_3)-$ |
| 271. | $OCH_3$ | $C_6H_5-CH_2-$ |
| 272. | $OCH_3$ | $4-(CH_3)_3C-C_6H_4-CH_2-$ |
| 273. | $OCH_3$ | $C_6H_5-CH_2-$ |
| 274. | $OCH_3$ | $4-(CH_3)_3C-C_6H_4-CH_2-$ |
| 275. | $OCH_3$ | $4-Cl-C_6H_4-CH_2-$ |
| 276. | $OCH_3$ | $3-(CH_3O)-C_6H_4-CH_2-$ |
| 277. | $OCH_3$ | $4-(CH_3O)-C_6H_4-CH_2-$ |
| 278. | $OCH_3$ | $2-(CH_3O)-C_6H_4-CH_2-$ |
| 279. | $OCH_3$ | $3-Cl-C_6H_4-CH_2-$ |
| 280. | $OCH_3$ | $2-Cl-C_6H_4-CH_2-$ |
| 281. | $OCH_3$ | $4-(F_3C)-C_6H_4-CH_2-$ |
| 282. | $OCH_3$ | $NC-CH_2-$ |
| 283. | $OCH_3$ | $NC-CH_2-CH_2-$ |
| 284. | $OCH_3$ | $NC-CH_2-CH(CH_3)-$ |
| 285. | $OCH_3$ | $NC-CH_2-C(CH_3)_2-$ |
| 286. | $OCH_3$ | $NC-CH_2-CH_2-CH_2-$ |
| 287. | $OCH_3$ | $FH_2C-CH_2-$ |
| 288. | $OCH_3$ | $ClH_2C-CH_2-$ |
| 289. | $OCH_3$ | $BrH_2C-CH_2-$ |
| 290. | $OCH_3$ | $FH_2C-CH(CH_3)-$ |
| 291. | $OCH_3$ | $ClH_2C-CH(CH_3)-$ |
| 292. | $OCH_3$ | $BrH_2C-CH(CH_3)-$ |
| 293. | $OCH_3$ | $F_2HC-CH_2-$ |
| 294. | $OCH_3$ | $F_3C-CH_2-$ |
| 295. | $OCH_3$ | $FH_2C-CH_2-CH_2-$ |
| 296. | $OCH_3$ | $ClH_2C-CH_2-CH_2-$ |
| 297. | $OCH_3$ | $BrH_2C-CH_2-CH_2-$ |
| 298. | $OCH_3$ | $F_2HC-CH_2-CH_2-$ |
| 299. | $OCH_3$ | $F_3C-CH_2-CH_2-$ |
| 300. | $OCH_3$ | $CH_3-O-CH_2-CH_2-$ |
| 301. | $OCH_3$ | $CH_3-S-CH_2-CH_2-$ |
| 302. | $OCH_3$ | $CH_3-SO_2-CH_2-CH_2-$ |
| 303. | $OCH_3$ | $C_2H_5-O-CH_2-CH_2-$ |
| 304. | $OCH_3$ | $(CH_3)_2CH-O-CH_2-CH_2-$ |
| 305. | $OCH_3$ | $C_2H_5-S-CH_2-CH_2-$ |
| 306. | $OCH_3$ | $C_2H_5SO_2-CH_2-CH_2-$ |
| 307. | $OCH_3$ | $(CH_3)_2N-CH_2-CH_2-$ |
| 308. | $OCH_3$ | $(C_2H_5)_2N-CH_2-CH_2-$ |
| 309. | $OCH_3$ | $[(CH_3)_2CH]_2N-CH_2-$ |
| 310. | $OCH_3$ | $CH_3-O-CH_2-CH(CH_3)-$ |
| 311. | $OCH_3$ | $CH_3-S-CH_2-CH(CH_3)-$ |
| 312. | $OCH_3$ | $CH_3-SO_2-CH_2-CH(CH_3)-$ |
| 313. | $OCH_3$ | $C_2H_5-O-CH_2-CH(CH_3)-$ |
| 314. | $OCH_3$ | $C_2H_5-S-CH_2-CH(CH_3)-$ |
| 315. | $OCH_3$ | $C_2H_5-SO_2-CH_2-CH(CH_3)-$ |
| 316. | $OCH_3$ | $(CH_3)_2N-CH_2-CH(CH_3)-$ |
| 317. | $OCH_3$ | $(C_2H_5)_2N-CH_2-CH(CH_3)-$ |
| 318. | $OCH_3$ | $[(CH_3)_2CH]_2N-CH_2-CH(CH_3)-$ |
| 319. | $OCH_3$ | $CH_3-O-CH(CH_3)-CH_2-$ |
| 320. | $OCH_3$ | $CH_3-S-CH(CH_3)-CH_2-$ |
| 321. | $OCH_3$ | $CH_3-SO_2-CH(CH_3)-CH_2-$ |
| 322. | $OCH_3$ | $C_2H_5-O-CH(CH_3)-CH_2-$ |
| 323. | $OCH_3$ | $C_2H_5-S-CH(CH_3)-CH_2-$ |
| 324. | $OCH_3$ | $C_2H_5-SO_2-CH(CH_3)-CH_2-$ |
| 325. | $OCH_3$ | $(CH_3)_2N-CH(CH_3)-CH_2-$ |
| 326. | $OCH_3$ | $(C_2H_5)_2N-CH(CH_3)-CH_2-$ |
| 327. | $OCH_3$ | $[(CH_3)_2CH]_2N-CH(CH_3)-CH_2-$ |
| 328. | $OCH_3$ | $CH_3-O-CH_2-CH_2-CH_2-$ |
| 329. | $OCH_3$ | $CH_3-S-CH_2-CH_2-CH_2-$ |

TABLE A-continued

| | R¹ | R² |
|---|---|---|
| 330. | OCH₃ | CH₃—SO₂—CH₂—CH₂—CH₂— |
| 331. | OCH₃ | C₂H₅—O—CH₂—CH₂—CH₂— |
| 332. | OCH₃ | C₂H₅—S—CH₂—CH₂—CH₂— |
| 333. | OCH₃ | C₂H₅—SO₂—CH₂—CH₂—CH₂— |
| 334. | OCH₃ | (CH₃)₂N—CH₂—CH₂—CH₂— |
| 335. | OCH₃ | (C₂H₅)₂N—CH₂—CH₂—CH₂— |
| 336. | OCH₃ | CH₃—O—CH₂—C(CH₃)₂— |
| 337. | OCH₃ | CH₃—S—CH₂—C(CH₃)₂— |
| 338. | OCH₃ | CH₃—SO₂—CH₂—C(CH₃)₂— |
| 339. | OCH₃ | C₂H₅—O—CH₂—C(CH₃)₂— |
| 340. | OCH₃ | C₂H₅—S—CH₂—C(CH₃)₂— |
| 341. | OCH₃ | C₂H₅—SO₂—CH₂—C(CH₃)₂— |
| 342. | OCH₃ | (CH₃)₂N—CH₂—C(CH₃)₂— |
| 343. | OCH₃ | (C₂H₅)₂N—CH₂—C(CH₃)₂— |
| 344. | OCH₃ | [(CH₃)₂CH]₂N—CH₂—C(CH₃)₂— |
| 345. | OCH₃ | Cl—CH₂—C≡C—CH₂— |
| 346. | OCH₃ | CH₃—O—C(O)—CH₂— |
| 347. | OCH₃ | C₂H₅—O—C(O)—CH₂— |
| 348. | OCH₃ | CH₃—O—C(O)—CH(CH₃) |
| 349. | OCH₃ | C₂H₅—O—C(O)—CH(CH₃) |
| 350. | OCH₃ | (CH₃O)₂CH—CH₂— |
| 351. | OCH₃ | (C₂H₅O)₂CH—CH₂— |
| 352. | OC₂H₅ | H |
| 353. | OC₂H₅ | CH₃ |
| 354. | OC₂H₅ | CH₃CH₂— |
| 355. | OC₂H₅ | (CH₃)₂CH— |
| 356. | OC₂H₅ | CH₃CH₂CH₂— |
| 357. | OC₂H₅ | n-C₄H₉ |
| 358. | OC₂H₅ | (CH₃)₃C— |
| 359. | OC₂H₅ | (CH₃)₂CH—CH₂— |
| 360. | OC₂H₅ | n-C₅H₁₁ |
| 361. | OC₂H₅ | (CH₃)₂CH—CH₂—CH₂— |
| 362. | OC₂H₅ | (C₂H₅)₂—CH— |
| 363. | OC₂H₅ | (CH₃)₃C—CH₂— |
| 364. | OC₂H₅ | (CH₃)₃C—CH₂—CH₂— |
| 365. | OC₂H₅ | C₂H₅CH(CH₃)—CH₂— |
| 366. | OC₂H₅ | CH₃—CH₂—C(CH₃)₂— |
| 367. | OC₂H₅ | (CH₃)₂CH—CH(CH₃)— |
| 368. | OC₂H₅ | (CH₃)₃C—CH(CH₃) |
| 369. | OC₂H₅ | (CH₃)₂CH—CH₂—CH(CH₃) |
| 370. | OC₂H₅ | CH₃—CH₂—C(CH₃)(C₂H₅)— |
| 371. | OC₂H₅ | CH₃—CH₂—CH₂—C(CH₃)₂— |
| 372. | OC₂H₅ | C₂H₅—CH₂—CH(CH₃)—CH₂— |
| 373. | OC₂H₅ | cyclopropyl |
| 374. | OC₂H₅ | cyclopropyl-CH₂— |
| 375. | OC₂H₅ | cyclopropyl-CH{CH₃}— |
| 376. | OC₂H₅ | cyclobutyl |
| 377. | OC₂H₅ | cyclopentyl |
| 378. | OC₂H₅ | cyclohexyl |
| 379. | OC₂H₅ | HC≡C—CH₂— |
| 380. | OC₂H₅ | HC≡C—CH(CH₃)— |
| 381. | OC₂H₅ | HC≡C—C(CH₃)₂— |
| 382. | OC₂H₅ | HC≡C—C(CH₃)(C₂H₅)— |
| 383. | OC₂H₅ | HC≡C—C(CH₃)(C₃H₇)— |
| 384. | OC₂H₅ | CH₂=CH—CH₂— |
| 385. | OC₂H₅ | H₂C=CH—CH(CH₃)— |
| 386. | OC₂H₅ | H₂C=CH—C(CH₃)₂— |
| 387. | OC₂H₅ | H₂C=CH—C(C₂H₅)(CH₃)— |
| 388. | OC₂H₅ | C₆H₅—CH₂— |
| 389. | OC₂H₅ | 4-(CH₃)₃C—C₆H₄—CH₂— |
| 390. | OC₂H₅ | C₆H₅—CH₂— |
| 391. | OC₂H₅ | 4-(CH₃)₃C—C₆H₄—CH₂— |
| 392. | OC₂H₅ | 4-Cl—C₆H₄—CH₂— |
| 393. | OC₂H₅ | 3-(CH₃O)—C₆H₄—CH₂— |
| 394. | OC₂H₅ | 4-(CH₃O)—C₆H₄—CH₂— |
| 395. | OC₂H₅ | 2-(CH₃O)—C₆H₄—CH₂— |
| 396. | OC₂H₅ | 3-Cl—C₆H₄—CH₂— |
| 397. | OC₂H₅ | 2-Cl—C₆H₄CH₂— |
| 398. | OC₂H₅ | 4-(F₃C)—C₆H₄—CH₂— |
| 399. | OC₂H₅ | NC—CH₂— |
| 400. | OC₂H₅ | NC—CH₂—CH₂— |
| 401. | OC₂H₅ | NC—CH₂—CH(CH₃)— |
| 402. | OC₂H₅ | NC—CH₂—C(CH₃)₂— |
| 403. | OC₂H₅ | NC—CH₂—CH₂—CH₂— |
| 404. | OC₂H₅ | FH₂C—CH₂— |
| 405. | OC₂H₅ | ClH₂C—CH₂— |
| 406. | OC₂H₅ | BrH₂C—CH₂— |
| 407. | OC₂H₅ | FH₂C—CH(CH₃)— |
| 408. | OC₂H₅ | ClH₂C—CH(CH₃)— |
| 409. | OC₂H₅ | BrH₂C—CH(CH₃)— |
| 410. | OC₂H₅ | F₂HC—CH₂— |
| 411. | OC₂H₅ | F₃C—CH₂— |
| 412. | OC₂H₅ | FH₂C—CH₂—CH₂— |
| 413. | OC₂H₅ | ClH₂C—CH₂—CH₂— |
| 414. | OC₂H₅ | BrH₂C—CH₂—CH₂— |
| 415. | OC₂H₅ | F₂HC—CH₂—CH₂— |
| 416. | OC₂H₅ | F₃C—CH₂—CH₂— |
| 417. | OC₂H₅ | CH₃—O—CH₂—CH₂— |
| 418. | OC₂H₅ | CH₃—S—CH₂—CH₂— |
| 419. | OC₂H₅ | CH₃—SO₂—CH₂—CH₂— |
| 420. | OC₂H₅ | C₂H₅—O—CH₂—CH₂— |
| 421. | OC₂H₅ | (CH₃)₂CH—O—CH₂—CH₂— |
| 422. | OC₂H₅ | C₂H₅—S—CH₂—CH₂— |
| 423. | OC₂H₅ | C₂H₅—SO₂—CH₂—CH₂— |
| 424. | OC₂H₅ | (CH₃)₂N—CH₂—CH₂— |
| 425. | OC₂H₅ | (C₂H₅)₂N—CH₂—CH₂— |
| 426. | OC₂H₅ | [(CH₃)₂CH]₂N—CH₂—CH₂— |
| 427. | OC₂H₅ | CH₃—O—CH₂—CH(CH₃)— |
| 428. | OC₂H₅ | CH₃—S—CH₂—CH(CH₃)— |
| 429. | OC₂H₅ | CH₃—SO₂—CH₂—CH(CH₃)— |
| 430. | OC₂H₅ | C₂H₅—O—CH₂—CH(CH₃)— |
| 431. | OC₂H₅ | C₂H₅—S—CH₂—CH(CH₃)— |
| 432. | OC₂H₅ | C₂H₅—SO₂—CH₂—CH(CH₃)— |
| 433. | OC₂H₅ | (CH₃)₂N—CH₂—CH(CH₃)— |
| 434. | OC₂H₅ | (C₂H₅)₂N—CH₂—CH(CH₃)— |
| 435. | OC₂H₅ | [(CH₃)₂CH]₂N—CH₂—CH{CH₃}— |
| 436. | OC₂H₅ | CH₃—O—CH(CH₃)—CH₂— |
| 437. | OC₂H₅ | CH₃—S—CH(CH₃)—CH₂— |
| 438. | OC₂H₅ | CH₃—SO₂—CH(CH₃)—CH₂— |
| 439. | OC₂H₅ | C₂H₅—O—CH(CH₃)—CH₂— |
| 440. | OC₂H₅ | C₂H₅—S—CH(CH₃)—CH₂— |
| 441. | OC₂H₅ | C₂H₅—SO₂—CH(CH₃)—CH₂— |
| 442. | OC₂H₅ | (CH₃)₂N—CH(CH₃)—CH₂— |
| 443. | OC₂H₅ | (C₂H₅)₂N—CH(CH₃)—CH₂— |
| 444. | OC₂H₅ | [(CH₃)₂CH]₂N—CH(CH₃)—CH₂— |
| 445. | OC₂H₅ | CH₃—O—CH₂—CH₂—CH₂— |
| 446. | OC₂H₅ | CH₃—S—CH₂—CH₂—CH₂— |
| 447. | OC₂H₅ | CH₃—SO₂—CH₂—CH₂—CH₂— |
| 448. | OC₂H₅ | C₂H₅—O—CH₂—CH₂—CH₂— |
| 449. | OC₂H₅ | C₂H₅—S—CH₂—CH₂—CH₂— |
| 450. | OC₂H₅ | C₂H₅—SO₂—CH₂—CH₂—CH₂— |
| 451. | OC₂H₅ | (CH₃)₂N—CH₂—CH₂—CH₂— |
| 452. | OC₂H₅ | (C₂H₅)₂N—CH₂—CH₂—CH₂— |
| 453. | OC₂H₅ | CH₃—O—CH₂—C(CH₃)₂— |
| 454. | OC₂H₅ | CH₃—S—CH₂—C(CH₃)₂— |
| 455. | OC₂H₅ | CH₃—SO₂—CH₂—C(CH₃)₂— |
| 456. | OC₂H₅ | C₂H₅—O—CH₂—C(CH₃)₂— |
| 457. | OC₂H₅ | C₂H₅—S—CH₂—C(CH₃)₂— |
| 458. | OC₂H₅ | C₂H₅—SO₂—CH₂—C(CH₃)₂— |
| 459. | OC₂H₅ | (CH₃)₂N—CH₂—C(CH₃)₂— |
| 460. | OC₂H₅ | (C₂H₅)₂N—CH₂—C(CH₃)₂— |
| 461. | OC₂H₅ | [(CH₃)₂CH]₂N—CH₂—C(CH₃)₂— |
| 462. | OC₂H₅ | Cl—CH₂—C≡C—CH₂— |
| 463. | OC₂H₅ | CH₃—O—C(O)—CH₂— |
| 464. | OC₂H₅ | C₂H₅—O—C(O)—CH₂— |
| 465. | OC₂H₅ | CH₃—O—C(O)—CH(CH₃) |
| 466. | OC₂H₅ | C₂H₅—O—C(O)—CH(CH₃) |
| 467. | OC₂H₅ | (CH₃O)₂CH—CH₂— |
| 468. | OC₂H₅ | (C₂H₅O)₂CH—CH₂— |
| 469. | CF₃ | H |
| 470. | CF₃ | CH₃ |
| 471. | CF₃ | CH₃CH₂— |
| 472. | CF₃ | (CH₃)₂CH— |
| 473. | CF₃ | CH₃CH₂CH₂— |
| 474. | CF₃ | n-C₄H₉ |
| 475. | CF₃ | (CH₃)₃C— |
| 476. | CF₃ | (CH₃)₂CH—CH₂— |
| 477. | CF₃ | n-C₅H₁₁ |
| 478. | CF₃ | (CH₃)₂CH—CH₂—CH₂— |
| 479. | CF₃ | (C₂H₅)₂—CH— |
| 480. | CF₃ | (CH₃)₃C—CH₂— |
| 481. | CF₃ | (CH₃)₃C—CH₂—CH₂— |
| 482. | CF₃ | C₂H₅CH(CH₃)—CH₂— |
| 483. | CF₃ | CH₃—CH₂—C(CH₃)₂— |
| 484. | CF₃ | (CH₃)₂CH—CH(CH₃)— |
| 485. | CF₃ | (CH₃)₃C—CH(CH₃)— |

TABLE A-continued

| | R¹ | R² |
|---|---|---|
| 486. | CF$_3$ | (CH$_3$)$_2$CH—CH$_2$—CH(CH$_3$)— |
| 487. | CF$_3$ | CH$_3$—CH$_2$—C(CH$_3$)(C$_2$H$_5$)— |
| 488. | CF$_3$ | CH$_3$—CH$_2$—CH$_2$—C(CH$_3$)$_2$— |
| 489.. | CF$_3$ | C$_2$H$_5$—CH$_2$—CH(CH$_3$)—CH$_2$— |
| 490. | CF$_3$ | cyclopropyl |
| 491. | CF$_3$ | cyclopropyl-CH$_2$— |
| 492. | CF$_3$ | cyclopropyl-CH{CH$_3$}— |
| 493. | CF$_3$ | cyclobutyl |
| 494. | CF$_3$ | cyclopentyl |
| 495. | CF$_3$ | cyclohexyl |
| 496. | CF$_3$ | HC≡C—CH$_2$— |
| 497. | CF$_3$ | HC≡C—CH(CH$_3$)— |
| 498. | CF$_3$ | HC≡C—C(CH$_3$)$_2$— |
| 499. | CF$_3$ | HC≡C—C(CH$_3$)(C$_2$H$_5$)— |
| 500. | CF$_3$ | HC≡C—C(CH$_3$)(C$_3$H$_7$)— |
| 501. | CF$_3$ | CH$_2$=CH—CH$_2$— |
| 502. | CF$_3$ | H$_2$C=CH—CH(CH$_3$)— |
| 503. | CF$_3$ | H$_2$C=CH—C(CH$_3$)$_2$— |
| 504. | CF$_3$ | H$_2$C=CH—C(C$_2$H$_5$)(CH$_3$)— |
| 505. | CF$_3$ | C$_6$H$_5$—CH$_2$— |
| 506. | CF$_3$ | 4-(CH$_3$)$_3$C—C$_6$H$_4$—CH$_2$— |
| 507. | CF$_3$ | C$_6$H$_5$—CH$_2$— |
| 508. | CF$_3$ | 4-(CH$_3$)$_3$C—C$_6$H$_4$—CH$_2$— |
| 509. | CF$_3$ | 4-Cl—C$_6$H$_4$—CH$_2$— |
| 510. | CF$_3$ | 3-(CH$_3$O)—C$_6$H$_4$—CH$_2$— |
| 511. | CF$_3$ | 4-(CH$_3$O)—C$_6$H$_4$—CH$_2$— |
| 512. | CF$_3$ | 2-(CH$_3$O)—C$_6$H$_4$—CH$_2$— |
| 513. | CF$_3$ | 3-Cl—C$_6$H$_4$—CH$_2$— |
| 514. | CF$_3$ | 2-Cl—C$_6$H$_4$CH$_2$— |
| 515. | CF$_3$ | 4-(F$_3$C)—C$_6$H$_4$—CH$_2$— |
| 516. | CF$_3$ | NC—CH$_2$— |
| 517. | CF$_3$ | NC—CH$_2$—CH$_2$— |
| 518. | CF$_3$ | NC—CH$_2$—CH(CH$_3$)— |
| 519. | CF$_3$ | NC—CH$_2$—C(CH$_3$)$_2$— |
| 520. | CF$_3$ | NC—CH$_2$—CH$_2$—CH$_2$— |
| 521. | CF$_3$ | FH$_2$C—CH$_2$— |
| 522. | CF$_3$ | ClH$_2$C—CH$_2$— |
| 523. | CF$_3$ | BrH$_2$C—CH$_2$— |
| 524. | CF$_3$ | FH$_2$C—CH(CH$_3$)— |
| 525. | CF$_3$ | ClH$_2$C—CH(CH$_3$)— |
| 526. | CF$_3$ | BrH$_2$C—CH(CH$_3$)— |
| 527. | CF$_3$ | F$_2$HC—CH$_2$— |
| 528. | CF$_3$ | F$_3$C—CH$_2$— |
| 529. | CF$_3$ | FH$_2$C—CH$_2$—CH$_2$— |
| 530. | CF$_3$ | ClH$_2$C—CH$_2$—CH$_2$— |
| 531. | CF$_3$ | BrH$_2$C—CH$_2$—CH$_2$— |
| 532. | CF$_3$ | F$_2$HC—CH$_2$—CH$_2$— |
| 533. | CF$_3$ | F$_3$C—CH$_2$—CH$_2$— |
| 534. | CF$_3$ | CH$_3$—O—CH$_2$—CH$_2$— |
| 535. | CF$_3$ | CH$_3$—S—CH$_2$—CH$_2$— |
| 536. | CF$_3$ | CH$_3$—SO$_2$—CH$_2$—CH$_2$— |
| 537. | CF$_3$ | C$_2$H$_5$—O—CH$_2$—CH$_2$— |
| 538. | CF$_3$ | (CH$_3$)$_2$CH—O—CH$_2$—CH$_2$— |
| 539. | CF$_3$ | C$_2$H$_5$—S—CH$_2$—CH$_2$— |
| 540. | CF$_3$ | C$_2$H$_5$—SO$_2$—CH$_2$—CH$_2$— |
| 541. | CF$_3$ | (CH$_3$)$_2$N—CH$_2$—CH$_2$— |
| 542. | CF$_3$ | (C$_2$H$_5$)$_2$N—CH$_2$—CH$_2$— |
| 543. | CF$_3$ | [(CH$_3$)$_2$CH]$_2$N—CH$_2$—CH$_2$— |
| 544. | CF$_3$ | CH$_3$—O—CH$_2$—CH(CH$_3$)— |
| 545. | CF$_3$ | CH$_3$—S—CH$_2$—CH(CH$_3$)— |
| 546. | CF$_3$ | CH$_3$—SO$_2$—CH$_2$—CH(CH$_3$)— |
| 547. | CF$_3$ | C$_2$H$_5$—O—CH$_2$—CH(CH$_3$)— |
| 548. | CF$_3$ | C$_2$H$_5$—S—CH$_2$—CH(CH$_3$)— |
| 549. | CF$_3$ | C$_2$H$_5$—SO$_2$—CH$_2$—CH(CH$_3$)— |
| 550. | CF$_3$ | (CH$_3$)$_2$N—CH$_2$—CH(CH$_3$)— |
| 551. | CF$_3$ | (C$_2$H$_5$)$_2$N—CH$_2$—CH(CH$_3$)— |
| 552. | CF$_3$ | [(CH$_3$)$_2$CH]$_2$N—CH$_2$—CH{CH$_3$}— |
| 553. | CF$_3$ | CH$_3$—O—CH(CH$_3$)—CH$_2$— |
| 554. | CF$_3$ | CH$_3$—S—CH(CH$_3$)—CH$_2$— |
| 555. | CF$_3$ | CH$_3$—SO$_2$—CH(CH$_3$)—CH$_2$— |
| 556. | CF$_3$ | C$_2$H$_5$—O—CH(CH$_3$)—CH$_2$— |
| 557. | CF$_3$ | C$_2$H$_5$—S—CH(CH$_3$)—CH$_2$— |
| 558. | CF$_3$ | C$_2$H$_5$—SO$_2$—CH(CH$_3$)—CH$_2$— |
| 559. | CF$_3$ | (CH$_3$)$_2$N—CH(CH$_3$)—CH$_2$— |
| 560. | CF$_3$ | (C$_2$H$_5$)$_2$N—CH(CH$_3$)—CH$_2$— |
| 561. | CF$_3$ | [(CH$_3$)$_2$CH]$_2$N—CH(CH$_3$)—CH$_2$— |
| 562. | CF$_3$ | CH$_3$—O—CH$_2$—CH$_2$—CH$_2$— |
| 563. | CF$_3$ | CH$_3$—S—CH$_2$—CH$_2$—CH$_2$— |
| 564. | CF$_3$ | CH$_3$—SO$_2$—CH$_2$—CH$_2$—CH$_2$— |
| 565. | CF$_3$ | C$_2$H$_5$—O—CH$_2$—CH$_2$—CH$_2$— |
| 566. | CF$_3$ | C$_2$H$_5$—S—CH$_2$—CH$_2$—CH$_2$— |
| 567. | CF$_3$ | C$_2$H$_5$—SO$_2$—CH$_2$—CH$_2$—CH$_2$— |
| 568. | CF$_3$ | (CH$_3$)$_2$N—CH$_2$—CH$_2$—CH$_2$— |
| 569. | CF$_3$ | (C$_2$H$_5$)$_2$N—CH$_2$—CH$_2$—CH$_2$— |
| 570. | CF$_3$ | CH$_3$—O—CH$_2$—C(CH$_3$)$_2$— |
| 571. | CF$_3$ | CH$_3$—S—CH$_2$—C(CH$_3$)$_2$— |
| 572. | CF$_3$ | CH$_3$—SO$_2$—CH$_2$—C(CH$_3$)$_2$— |
| 573. | CF$_3$ | C$_2$H$_5$—O—CH$_2$—C(CH$_3$)$_2$— |
| 574. | CF$_3$ | C$_2$H$_5$—S—CH$_2$—C(CH$_3$)$_2$— |
| 575. | CF$_3$ | C$_2$H$_5$—SO$_2$—CH$_2$—C(CH$_3$)$_2$— |
| 576. | CF$_3$ | (CH$_3$)$_2$N—CH$_2$—C(CH$_3$)$_2$— |
| 577. | CF$_3$ | (C$_2$H$_5$)$_2$N—CH$_2$—C(CH$_3$)$_2$— |
| 578. | CF$_3$ | [(CH$_3$)$_2$CH]$_2$N—CH$_2$—C(CH$_3$)$_2$— |
| 579. | CF$_3$ | Cl—CH$_2$—C≡C—CH$_2$— |
| 580. | CF$_3$ | CH$_3$—O—C(O)—CH$_2$ |
| 581. | CF$_3$ | C$_2$H$_5$—O—C(O)—CH$_2$ |
| 582. | CF$_3$ | CH$_3$—O—C(O)—CH(CH$_3$) |
| 583. | CF$_3$ | C$_2$H$_5$—O—C(O)—CH(CH$_3$) |
| 584. | CF$_3$ | (CH$_3$—O)$_2$CH—CH$_2$— |
| 585. | CF$_3$ | (C$_2$H$_5$O)$_2$CH—CH$_2$— |
| 586. | OCHF$_2$ | H |
| 587. | OCHF$_2$ | CH$_3$ |
| 588. | OCHF$_2$ | CH$_3$CH$_2$— |
| 589. | OCHF$_2$ | (CH$_3$)$_2$CH— |
| 590. | OCHF$_2$ | CH$_3$CH$_2$CH$_2$— |
| 591. | OCHF$_2$ | n-C$_4$H$_9$ |
| 592. | OCHF$_2$ | (CH$_3$)$_3$C— |
| 593. | OCHF$_2$ | (CH$_3$)$_2$CH—CH$_2$— |
| 594. | OCHF$_2$ | n-C$_5$H$_{11}$ |
| 595. | OCHF$_2$ | (CH$_3$)$_2$CH—CH$_2$—CH$_2$— |
| 596. | OCHF$_2$ | (C$_2$H$_5$)$_2$—CH— |
| 597. | OCHF$_2$ | (CH$_3$)$_3$C—CH$_2$— |
| 598. | OCHF$_2$ | (CH$_3$)$_3$C—CH$_2$—CH$_2$— |
| 599. | OCHF$_2$ | C$_2$H$_5$CH(CH$_3$)—CH$_2$— |
| 600. | OCHF$_2$ | CH$_3$—CH$_2$—C(CH$_3$)$_2$— |
| 601. | OCHF$_2$ | (CH$_3$)$_2$CH—CH(CH$_3$)— |
| 602. | OCHF$_2$ | (CH$_3$)$_3$C—CH(CH$_3$)— |
| 603. | OCHF$_2$ | (CH$_3$)$_2$CH—CH$_2$—CH(CH$_3$) |
| 604. | OCHF$_2$ | CH$_3$CH$_2$—C(CH$_3$)(C$_2$H$_5$)— |
| 605. | OCHF$_2$ | CH$_3$—CH$_2$—CH$_2$—C(CH$_3$)$_2$— |
| 606. | OCHF$_2$ | C$_2$H$_5$—CH$_2$—CH(CH$_3$)—CH$_2$— |
| 607. | OCHF$_2$ | cyclopropyl |
| 608. | OCHF$_2$ | cyclopropyl-CH$_2$— |
| 609. | OCHF$_2$ | cyclopropyl-CH(CH$_3$)— |
| 610. | OCHF$_2$ | cyclobutyl |
| 611. | OCHF$_2$ | cyclopentyl |
| 612. | OCHF$_2$ | cyclohexyl |
| 613. | OCHF$_2$ | HC≡C—CH$_2$— |
| 614. | OCHF$_2$ | HC≡C—CH(CH$_3$)— |
| 615. | OCHF$_2$ | HC≡C—C(CH$_3$)$_2$— |
| 616. | OCHF$_2$ | HC≡C—C(CH$_3$)(C$_2$H$_5$)— |
| 617. | OCHF$_2$ | HC≡C—C(CH$_3$)(C$_3$H$_7$)— |
| 618. | OCHF$_2$ | CH$_2$=CH—CH$_2$— |
| 619. | OCHF$_2$ | H$_2$C=CH—CH(CH$_3$)— |
| 620. | OCHF$_2$ | H$_2$C=CH—C(CH$_3$)$_2$— |
| 621. | OCHF$_2$ | H$_2$C=CH—C(C$_2$H$_5$)(CH$_3$)— |
| 622. | OCHF$_2$ | C$_6$H$_5$—CH$_2$— |
| 623. | OCHF$_2$ | 4-(CH$_3$)$_3$C—C$_6$H$_4$—CH$_2$— |
| 624. | OCHF$_2$ | C$_6$H$_5$—CH$_2$— |
| 625. | OCHF$_2$ | 4-(CH$_3$)$_3$C—C$_6$H$_4$—CH$_2$— |
| 626. | OCHF$_2$ | 4-Cl—C$_6$H$_4$—CH$_2$— |
| 627. | OCHF$_2$ | 3-(CH$_3$O)—C$_6$H$_4$—CH$_2$— |
| 628. | OCHF$_2$ | 4-(CH$_3$O)—C$_6$H$_4$—CH$_2$— |
| 629. | OCHF$_2$ | 2-(CH$_3$O)—C$_6$H$_4$—CH$_2$— |
| 630. | OCHF$_2$ | 3-Cl—C$_6$H$_4$—CH$_2$— |
| 631. | OCHF$_2$ | 2-Cl—C$_6$H$_4$CH$_2$— |
| 632. | OCHF$_2$ | 4-(F$_3$C)—C$_6$H$_4$—CH$_2$— |
| 633. | OCHF$_2$ | NC—CH$_2$— |
| 634. | OCHF$_2$ | NC—CH$_2$—CH$_2$— |
| 635. | OCHF$_2$ | NC—CH$_2$—CH(CH$_3$)— |
| 636. | OCHF$_2$ | NC—CH$_2$—C(CH$_3$)$_2$— |
| 637. | OCHF$_2$ | NC—CH$_2$—CH$_2$—CH$_2$— |
| 638. | OCHF$_2$ | FH$_2$C—CH$_2$— |
| 639. | OCHF$_2$ | ClH$_2$C—CH$_2$— |
| 640. | OCHF$_2$ | BrH$_2$C—CH$_2$— |
| 641. | OCHF$_2$ | FH$_2$C—CH(CH$_3$)— |

TABLE A-continued

| | R¹ | R² |
|---|---|---|
| 642. | OCHF$_2$ | ClH$_2$C—CH(CH$_3$)— |
| 643. | OCHF$_2$ | BrH$_2$C—CH(CH$_3$)— |
| 644. | OCHF$_2$ | F$_2$HC—CH$_2$— |
| 645. | OCHF$_2$ | F$_3$C—CH$_2$— |
| 646. | OCHF$_2$ | FH$_2$C—CH$_2$—CH$_2$— |
| 647. | OCHF$_2$ | ClH$_2$C—CH$_2$—CH$_2$— |
| 648. | OCHF$_2$ | BrH$_2$C—CH$_2$—CH$_2$— |
| 649. | OCHF$_2$ | F$_2$HC—CH$_2$—CH$_2$— |
| 650. | OCHF$_2$ | F$_3$C—CH$_2$—CH$_2$— |
| 651. | OCHF$_2$ | CH$_3$—O—CH$_2$—CH$_2$— |
| 652. | OCHF$_2$ | CH$_3$—S—CH$_2$—CH$_2$— |
| 653. | OCHF$_2$ | CH$_3$—SO$_2$—CH$_2$—CH$_2$— |
| 654. | OCHF$_2$ | C$_2$H$_5$—O—CH$_2$—CH$_2$— |
| 655. | OCHF$_2$ | (CH$_3$)$_2$CH—O—CH$_2$—CH$_2$— |
| 656. | OCHF$_2$ | C$_2$H$_5$—S—CH$_2$—CH$_2$— |
| 657. | OCHF$_2$ | C$_2$H$_5$—SO$_2$—CH$_2$—CH$_2$— |
| 658. | OCHF$_2$ | (CH$_3$)$_2$N—CH$_2$—CH$_2$— |
| 659. | OCHF$_2$ | (C$_2$H$_5$)$_2$N—CH$_2$—CH$_2$— |
| 660. | OCHF$_2$ | [(CH$_3$)$_2$CH]$_2$N—CH$_2$—CH$_2$— |
| 661. | OCHF$_2$ | CH$_3$—O—CH$_2$—CH(CH$_3$)— |
| 662. | OCHF$_2$ | CH$_3$—S—CH$_2$—CH(CH$_3$)— |
| 663. | OCHF$_2$ | CH$_3$—SO$_2$—CH$_2$—CH(CH$_3$)— |
| 664. | OCHF$_2$ | C$_2$H$_5$—O—CH$_2$—CH(CH$_3$)— |
| 665. | OCHF$_2$ | C$_2$H$_5$—S—CH$_2$—CH(CH$_3$)— |
| 666. | OCHF$_2$ | C$_2$H$_5$—SO$_2$—CH$_2$—CH(CH$_3$)— |
| 667. | OCHF$_2$ | (CH$_3$)$_2$N—CH$_2$—CH(CH$_3$)— |
| 668. | OCHF$_2$ | (C$_2$H$_5$)$_2$N—CH$_2$—CH(CH$_3$)— |
| 669. | OCHF$_2$ | [(CH$_3$)$_2$CH]$_2$N—CH$_2$—CH(CH$_3$)— |
| 670. | OCHF$_2$ | CH$_3$—O—CH(CH$_3$)—CH$_2$— |
| 671. | OCHF$_2$ | CH$_3$—S—CH(CH$_3$)—CH$_2$— |
| 672. | OCHF$_2$ | CH$_3$—SO$_2$—CH(CH$_3$)—CH$_2$— |
| 673. | OCHF$_2$ | C$_2$H$_5$—O—CH(CH$_3$)—CH$_2$— |
| 674. | OCHF$_2$ | C$_2$H$_5$—S—CH(CH$_3$)—CH$_2$— |
| 675. | OCHF$_2$ | C$_2$H$_5$—SO$_2$—CH(CH$_3$)—CH$_2$— |
| 676. | OCHF$_2$ | (CH$_3$)$_2$N—CH(CH$_3$)—CH$_2$— |
| 677. | OCHF$_2$ | (C$_2$H$_5$)$_2$N—CH(CH$_3$)—CH$_2$— |
| 678. | OCHF$_2$ | [(CH$_3$)$_2$CH]$_2$N—CH(CH$_3$)—CH$_2$— |
| 679. | OCHF$_2$ | CH$_3$—O—CH$_2$—CH$_2$—CH$_2$— |
| 680. | OCHF$_2$ | CH$_3$—S—CH$_2$—CH$_2$—CH$_2$— |
| 681. | OCHF$_2$ | CH$_3$—SO$_2$—CH$_2$—CH$_2$—CH$_2$— |
| 682. | OCHF$_2$ | C$_2$H$_5$—O—CH$_2$—CH$_2$—CH$_2$— |
| 683. | OCHF$_2$ | C$_2$H$_5$—S—CH$_2$—CH$_2$—CH$_2$— |
| 684. | OCHF$_2$ | C$_2$H$_5$—SO$_2$—CH$_2$—CH$_2$—CH$_2$— |
| 685. | OCHF$_2$ | (CH$_3$)$_2$N—CH$_2$—CH$_2$—CH$_2$— |
| 686. | OCHF$_2$ | (C$_2$H$_5$)$_2$N—CH$_2$—CH$_2$—CH$_2$— |
| 687. | OCHF$_2$ | CH$_3$—O—CH$_2$—C(CH$_3$)$_2$— |
| 688. | OCHF$_2$ | CH$_3$—S—CH$_2$—C(CH$_3$)$_2$— |
| 689. | OCHF$_2$ | CH$_3$—SO$_2$—CH$_2$—C(CH$_3$)$_2$— |
| 690. | OCHF$_2$ | C$_2$H$_5$—O—CH$_2$—C(CH$_3$)$_2$— |
| 691. | OCHF$_2$ | C$_2$H$_5$—S—CH$_2$—C(CH$_3$)$_2$— |
| 692. | OCHF$_2$ | C$_2$H$_5$—SO$_2$—CH$_2$—C(CH$_3$)$_2$— |
| 693. | OCHF$_2$ | (CH$_3$)$_2$N—CH$_2$—C(CH$_3$)$_2$— |
| 694. | OCHF$_2$ | (C$_2$H$_5$)$_2$N—CH$_2$—C(CH$_3$)$_2$— |
| 695. | OCHF$_2$ | [(CH$_3$)$_2$CH]$_2$N—CH$_2$—C(CH$_3$)$_2$— |
| 696. | OCHF$_2$ | Cl—CH$_2$—C≡C—CH$_2$— |
| 697. | OCHF$_2$ | CH$_3$—O—C(O)—CH$_2$ |
| 698. | OCHF$_2$ | C$_2$H$_5$—O—C(O)—CH$_2$ |
| 699. | OCHF$_2$ | CH$_3$—O—C(O)—CH(CH$_3$)— |
| 700. | OCHF$_2$ | C$_2$H$_5$—O—C(O)—CH(CH$_3$)— |
| 701. | OCHF$_2$ | (CH$_3$O)$_2$CH—CH$_2$— |
| 702. | OCHF$_2$ | (C$_2$H$_5$O)$_2$CH—CH$_2$— |
| 703. | OCF$_3$ | H |
| 704. | OCF$_3$ | CH$_3$ |
| 705. | OCF$_3$ | CH$_3$CH$_2$— |
| 706. | OCF$_3$ | (CH$_3$)$_2$CH— |
| 707. | OCF$_3$ | CH$_3$CH$_2$CH$_2$— |
| 708. | OCF$_3$ | n-C$_4$H$_9$ |
| 709. | OCF$_3$ | (CH$_3$)$_3$C— |
| 710. | OCF$_3$ | (CH$_3$)$_2$CH—CH$_2$— |
| 711. | OCF$_3$ | n-C$_5$H$_{11}$ |
| 712. | OCF$_3$ | (CH$_3$)$_2$CH—CH$_2$—CH$_2$— |
| 713. | OCF$_3$ | (C$_2$H$_5$)$_2$—CH— |
| 714. | OCF$_3$ | (CH$_3$)$_3$C—CH$_2$— |
| 715. | OCF$_3$ | (CH$_3$)$_3$C—CH$_2$—CH$_2$— |
| 716. | OCF$_3$ | C$_2$H$_5$CH(CH$_3$)—CH$_2$— |
| 717. | OCF$_3$ | CH$_3$—CH$_2$—C(CH$_3$)$_2$— |
| 718. | OCF$_3$ | (CH$_3$)$_2$CH—CH(CH$_3$)— |
| 719. | OCF$_3$ | (CH$_3$)$_3$C—CH(CH$_3$)— |
| 720. | OCF$_3$ | (CH$_3$)$_2$CH—CH$_2$—CH(CH$_3$)— |
| 721. | OCF$_3$ | CH$_3$—CH$_2$—C(CH$_3$)(C$_2$H$_5$)— |
| 722. | OCF$_3$ | CH$_3$—CH$_2$—CH$_2$—C(CH$_3$)$_2$— |
| 723. | OCF$_3$ | C$_2$H$_5$—CH$_2$—CH(CH$_3$)—CH$_2$— |
| 724. | OCF$_3$ | cyclopropyl |
| 725. | OCF$_3$ | cyclopropyl-CH$_2$— |
| 726. | OCF$_3$ | cyclopropyl-CH(CH$_3$)— |
| 727. | OCF$_3$ | cyclobutyl |
| 728. | OCF$_3$ | cyclopentyl |
| 729. | OCF$_3$ | cyclohexyl |
| 730. | OCF$_3$ | HC≡C—CH$_2$— |
| 731. | OCF$_3$ | HC≡C—CH(CH$_3$)— |
| 732. | OCF$_3$ | HC≡C—C(CH$_3$)$_2$— |
| 733. | OCF$_3$ | HC≡C—C(CH$_3$)(C$_2$H$_5$)— |
| 734. | OCF$_3$ | HC≡C—C(CH$_3$)(C$_3$H$_7$)— |
| 735. | OCF$_3$ | CH$_2$=CH—CH$_2$— |
| 736. | OCF$_3$ | H$_2$C=CH—CH(CH$_3$)— |
| 737. | OCF$_3$ | H$_2$C=CH—C(CH$_3$)$_2$— |
| 738. | OCF$_3$ | H$_2$C=CH—C(C$_2$H$_5$)(CH$_3$)— |
| 739. | OCF$_3$ | C$_6$H$_5$—CH$_2$— |
| 740. | OCF$_3$ | 4-(CH$_3$)$_3$C—C$_6$H$_4$—CH$_2$— |
| 741. | OCF$_3$ | C$_6$H$_5$—CH$_2$— |
| 742. | OCF$_3$ | 4-(CH$_3$)$_3$C—C$_6$H$_4$—CH$_2$— |
| 743. | OCF$_3$ | 4-Cl—C$_6$H$_4$—CH$_2$— |
| 744. | OCF$_3$ | 3-(CH$_3$O)—C$_6$H$_4$—CH$_2$— |
| 745. | OCF$_3$ | 4-(CH$_3$O)—C$_6$H$_4$—CH$_2$— |
| 746. | OCF$_3$ | 2-(CH$_3$O)—C$_6$H$_4$—CH$_2$— |
| 747. | OCF$_3$ | 3-Cl—C$_6$H$_4$—CH$_2$— |
| 748. | OCF$_3$ | 2-Cl—C$_6$H$_4$—CH$_2$— |
| 749. | OCF$_3$ | 4-(F$_3$C)—C$_6$H$_4$—CH$_2$— |
| 750. | OCF$_3$ | NC—CH$_2$— |
| 751. | OCF$_3$ | NC—CH$_2$—CH$_2$— |
| 752. | OCF$_3$ | NC—CH$_2$—CH(CH$_3$)— |
| 753. | OCF$_3$ | NC—CH$_2$—C(CH$_3$)$_2$— |
| 754. | OCF$_3$ | NC—CH$_2$—CH$_2$—CH$_2$— |
| 755. | OCF$_3$ | FH$_2$C—CH$_2$— |
| 756. | OCF$_3$ | ClH$_2$C—CH$_2$— |
| 757. | OCF$_3$ | BrH$_2$C—CH$_2$— |
| 758. | OCF$_3$ | FH$_2$C—CH(CH$_3$)— |
| 759. | OCF$_3$ | ClH$_2$C—CH(CH$_3$)— |
| 760. | OCF$_3$ | BrH$_2$C—CH(CH$_3$)— |
| 761. | OCF$_3$ | F$_2$HC—CH$_2$— |
| 762. | OCF$_3$ | F$_3$C—CH$_2$— |
| 763. | OCF$_3$ | FH$_2$C—CH$_2$—CH$_2$— |
| 764. | OCF$_3$ | ClH$_2$C—CH$_2$—CH$_2$— |
| 765. | OCF$_3$ | BrH$_2$C—CH$_2$—CH$_2$— |
| 766. | OCF$_3$ | F$_2$HC—CH$_2$—CH$_2$— |
| 767. | OCF$_3$ | F$_3$C—CH$_2$—CH$_2$— |
| 768. | OCF$_3$ | CH$_3$—O—CH$_2$—CH$_2$— |
| 769. | OCF$_3$ | CH$_3$—S—CH$_2$—CH$_2$— |
| 770. | OCF$_3$ | CH$_3$—SO$_2$—CH$_2$—CH$_2$— |
| 771. | OCF$_3$ | C$_2$H$_5$—O—CH$_2$—CH$_2$— |
| 772. | OCF$_3$ | (CH$_3$)$_2$CH—O—CH$_2$—CH$_2$— |
| 773. | OCF$_3$ | C$_2$H$_5$—S—CH$_2$—CH$_2$— |
| 774. | OCF$_3$ | C$_2$H$_5$SO$_2$—CH$_2$—CH$_2$— |
| 775. | OCF$_3$ | (CH$_3$)$_2$N—CH$_2$—CH$_2$— |
| 776. | OCF$_3$ | (C$_2$H$_5$)$_2$N—CH$_2$—CH$_2$— |
| 777. | OCF$_3$ | [(CH$_3$)$_2$CH]$_2$N—CH$_2$CH$_2$— |
| 778. | OCF$_3$ | CH$_3$—O—CH$_2$—CH(CH$_3$)— |
| 779. | OCF$_3$ | CH$_3$—S—CH$_2$—CH(CH$_3$)— |
| 780. | OCF$_3$ | CH$_3$—SO$_2$—CH$_2$—CH(CH$_3$)— |
| 781. | OCF$_3$ | C$_2$H$_5$—O—CH$_2$—CH(CH$_3$)— |
| 782. | OCF$_3$ | C$_2$H$_5$—S—CH$_2$—CH(CH$_3$)— |
| 783. | OCF$_3$ | C$_2$H$_5$—SO$_2$—CH$_2$—CH(CH$_3$)— |
| 784. | OCF$_3$ | (CH$_3$)$_2$N—CH$_2$—CH(CH$_3$)— |
| 785. | OCF$_3$ | (C$_2$H$_5$)$_2$N—CH$_2$—CH(CH$_3$)— |
| 786. | OCF$_3$ | [(CH$_3$)$_2$CH]$_2$N—CH$_2$—CH(CH$_3$)— |
| 787. | OCF$_3$ | CH$_3$—O—CH(CH$_3$)—CH$_2$— |
| 788. | OCF$_3$ | CH$_3$—S—CH(CH$_3$)—CH$_2$— |
| 789. | OCF$_3$ | CH$_3$—SO$_2$—CH(CH$_3$)—CH$_2$— |
| 790. | OCF$_3$ | C$_2$H$_5$—O—CH(CH$_3$)—CH$_2$— |
| 791. | OCF$_3$ | C$_2$H$_5$—S—CH(CH$_3$)—CH$_2$— |
| 792. | OCF$_3$ | C$_2$H$_5$—SO$_2$—CH(CH$_3$)—CH$_2$— |
| 793. | OCF$_3$ | (CH$_3$)$_2$N—CH(CH$_3$)—CH$_2$— |
| 794. | OCF$_3$ | (C$_2$H$_5$)$_2$N—CH(CH$_3$)—CH$_2$— |
| 795. | OCF$_3$ | [(CH$_3$)$_2$CH]$_2$N—CH(CH$_3$)—CH$_2$— |
| 796. | OCF$_3$ | CH$_3$—O—CH$_2$—CH$_2$—CH$_2$— |
| 797. | OCF$_3$ | CH$_3$—S—CH$_2$—CH$_2$—CH$_2$— |

TABLE A-continued

| | R¹ | R² |
|---|---|---|
| 798. | OCF₃ | CH₃—SO₂—CH₂—CH₂—CH₂— |
| 799. | OCF₃ | C₂H₅—O—CH₂—CH₂—CH₂— |
| 800. | OCF₃ | C₂H₅—S—CH₂—CH₂—CH₂— |
| 801. | OCF₃ | C₂H₅—SO₂—CH₂—CH₂—CH₂— |
| 802. | OCF₃ | (CH₃)₂N—CH₂—CH₂—CH₂— |
| 803. | OCF₃ | (C₂H₅)₂N—CH₂—CH₂—CH₂— |
| 804. | OCF₃ | CH₃—O—CH₂—C(CH₃)₂— |
| 805. | OCF₃ | CH₃—S—CH₂—C(CH₃)₂— |
| 806. | OCF₃ | CH₃—SO₂—CH₂—C(CH₃)₂— |
| 807. | OCF₃ | C₂H₅—O—CH₂—C(CH₃)₂— |
| 808. | OCF₃ | C₂H₅—S—CH₂—C(CH₃)₂— |
| 809. | OCF₃ | C₂H₅—SO₂—CH₂—C(CH₃)₂— |
| 810. | OCF₃ | (CH₃)₂N—CH₂—C(CH₃)₂— |
| 811. | OCF₃ | (C₂H₅)₂N—CH₂—C(CH₃)₂— |
| 812. | OCF₃ | [(CH₃)₂CH]₂N—CH₂—C(CH₃)₂— |
| 813. | OCF₃ | Cl—CH₂—C≡C—CH₂— |
| 814. | OCF₃ | CH₃—O—C(O)—CH₂ |
| 815. | OCF₃ | C₂H₅—O—C(O)—CH₂ |
| 816. | OCF₃ | CH₃—O—C(O)—CH(CH₃)— |
| 817. | OCF₃ | C₂H₅—O—C(O)—CH(CH₃)— |
| 818. | OCF₃ | (CH₃O)₂CH—CH₂— |
| 819. | OCF₃ | (C₂H₅O)₂CH—CH₂— |
| 820. | OCClF₂ | H |
| 821. | OCClF₂ | CH₃ |
| 822. | OCClF₂ | CH₃CH₂— |
| 823. | OCClF₂ | (CH₃)₂CH— |
| 824. | OCClF₂ | CH₃CH₂CH₂— |
| 825. | OCClF₂ | n-C₄H₉ |
| 826. | OCClF₂ | (CH₃)₃C— |
| 827. | OCClF₂ | (CH₃)₂CH—CH₂— |
| 828. | OCClF₂ | n-C₅H₁₁ |
| 829. | OCClF₂ | (CH₃)₂CH—CH₂—CH₂— |
| 830. | OCClF₂ | (C₂H₅)₂—CH— |
| 831. | OCClF₂ | (CH₃)₃C—CH₂— |
| 832. | OCClF₂ | (CH₃)₃C—CH₂—CH₂— |
| 833. | OCClF₂ | C₂H₅CH(CH₃)—CH₂— |
| 834. | OCClF₂ | CH₃—CH₂—C(CH₃)₂— |
| 835. | OCClF₂ | (CH₃)₂CH—CH(CH₃)— |
| 836. | OCClF₂ | (CH₃)₃C—CH(CH₃)— |
| 837. | OCClF₂ | (CH₃)₂CH—CH₂—CH(CH₃) |
| 838. | OCClF₂ | CH₃CH₂—C(CH₃)(C₂H₅)— |
| 839. | OCClF₂ | CH₃—CH₂—CH₂—C(CH₃)₂— |
| 840. | OCClF₂ | C₂H₅—CH₂—CH(CH₃)—CH₂— |
| 841. | OCClF₂ | cyclopropyl |
| 842. | OCClF₂ | cyclopropyl-CH₂— |
| 843. | OCClF₂ | cyclopropyl-CH(CH₃)— |
| 844. | OCClF₂ | cyclobutyl |
| 845. | OCClF₂ | cyclopentyl |
| 846. | OCClF₂ | cyclohexyl |
| 847. | OCClF₂ | HC≡C—CH₂— |
| 848. | OCClF₂ | HC≡C—CH(CH₃)— |
| 849. | OCClF₂ | HC≡C—C(CH₃)₂— |
| 850. | OCClF₂ | HC≡C—C(CH₃)(C₂H₅)— |
| 851. | OCClF₂ | HC≡C—C(CH₃)(C₃H₇)— |
| 852. | OCClF₂ | CH₂═CH—CH₂— |
| 853. | OCClF₂ | H₂C═CH—CH(CH₃)— |
| 854. | OCClF₂ | H₂C═CH—C(CH₃)₂— |
| 855. | OCClF₂ | H₂C═CH—C(C₂H₅)(CH₃)— |
| 856. | OCClF₂ | C₆H₅—CH₂— |
| 857. | OCClF₂ | 4-(CH₃)₃C—C₆H₄—CH₂— |
| 858. | OCClF₂ | C₆H₅—CH₂— |
| 859. | OCClF₂ | 4-(CH₃)₃C—C₆H₄—CH₂— |
| 860. | OCClF₂ | 4-Cl—C₆H₄—CH₂— |
| 861. | OCClF₂ | 3-(CH₃O)—C₆H₄—CH₂— |
| 862. | OCClF₂ | 4-(CH₃O)—C₆H₄—CH₂— |
| 863. | OCClF₂ | 2-(CH₃O)—C₆H₄—CH₂— |
| 864. | OCClF₂ | 3-Cl—C₆H₄—CH₂— |
| 865. | OCClF₂ | 2-Cl—C₆H₄—CH₂— |
| 866. | OCClF₂ | 4-(F₃C)—C₆H₄—CH₂— |
| 867. | OCClF₂ | NC—CH₂— |
| 868. | OCClF₂ | NC—CH₂—CH₂— |
| 869. | OCClF₂ | NC—CH₂—CH(CH₃)— |
| 870. | OCClF₂ | NC—CH₂—C(CH₃)₂— |
| 871. | OCClF₂ | NC—CH₂—CH₂—CH₂— |
| 872. | OCClF₂ | FH₂C—CH₂— |
| 873. | OCClF₂ | ClH₂C—CH₂— |
| 874. | OCClF₂ | BrH₂C—CH₂— |
| 875. | OCClF₂ | FH₂C—CH(CH₃)— |
| 876. | OCClF₂ | ClH₂C—CH(CH₃)— |
| 877. | OCClF₂ | BrH₂C—CH(CH₃)— |
| 878. | OCClF₂ | F₂HC—CH₂— |
| 879. | OCClF₂ | F₃C—CH₂— |
| 880. | OCClF₂ | FH₂C—CH₂—CH₂— |
| 881. | OCClF₂ | ClH₂C—CH₂—CH₂— |
| 882. | OCClF₂ | BrH₂C—CH₂—CH₂— |
| 883. | OCClF₂ | F₂HC—CH₂—CH₂— |
| 884. | OCClF₂ | F₃C—CH₂—CH₂— |
| 885. | OCClF₂ | CH₃—O—CH₂—CH₂— |
| 886. | OCClF₂ | CH₃—S—CH₂—CH₂— |
| 887. | OCClF₂ | CH₃—SO₂—CH₂—CH₂— |
| 888. | OCClF₂ | C₂H₅—O—CH₂—CH₂— |
| 889. | OCClF₂ | (CH₃)₂CH—O—CH₂—CH₂— |
| 890. | OCClF₂ | C₂H₅—S—CH₂—CH₂— |
| 891. | OCClF₂ | C₂H₅SO₂—CH₂—CH₂— |
| 892. | OCClF₂ | (CH₃)₂N—CH₂—CH₂— |
| 893. | OCClF₂ | (C₂H₅)₂N—CH₂—CH₂— |
| 894. | OCClF₂ | [(CH₃)₂CH]₂N—CH,CH₂— |
| 895. | OCClF₂ | CH₃—O—CH₂—CH(CH₃)— |
| 896. | OCClF₂ | CH₃—S—CH₂—CH(CH₃)— |
| 897. | OCClF₂ | CH₃—SO₂—CH₂—CH(CH₃)— |
| 898. | OCClF₂ | C₂H₅—O—CH₂—CH(CH₃)— |
| 899. | OCClF₂ | C₂H₅—S—CH₂—CH(CH₃)— |
| 900. | OCClF₂ | C₂H₅—SO₂—CH₂—CH(CH₃)— |
| 901. | OCClF₂ | (CH₃)₂N—CH₂—CH(CH₃)— |
| 902. | OCClF₂ | (C₂H₅)₂N—CH₂—CH(CH₃)— |
| 903. | OCClF₂ | [(CH₃)₂CH]₂N—CH₂—CH(CH₃)— |
| 904. | OCClF₂ | CH₃—O—CH(CH₃)—CH₂— |
| 905. | OCClF₂ | CH₃—S—CH(CH₃)—CH₂— |
| 906. | OCClF₂ | CH₃—SO₂—CH(CH₃)—CH₂— |
| 907. | OCClF₂ | C₂H₅—O—CH(CH₃)—CH₂— |
| 908. | OCClF₂ | C₂H₅—S—CH(CH₃)—CH₂— |
| 909. | OCClF₂ | C₂H₅—SO₂—CH(CH₃)—CH₂— |
| 910. | OCClF₂ | (CH₃)—N—CH(CH₃)—CH₂— |
| 911. | OCClF₂ | (C₂H₅)₂—N—CH(CH₃)—CH₂— |
| 912. | OCClF₂ | [(CH₃)₂CH]₂N—CH(CH₃)—CH₂— |
| 913. | OCClF₂ | CH₃—O—CH₂—CH₂—CH₂— |
| 914. | OCClF₂ | CH₃—S—CH₂—CH₂—CH₂— |
| 915. | OCClF₂ | CH₃—SO₂—CH₂—CH₂—CH₂— |
| 916. | OCClF₂ | C₂H₅—O—CH₂—CH₂—CH₂— |
| 917. | OCClF₂ | C₂H₅—S—CH₂—CH₂—CH₂— |
| 918. | OCClF₂ | C₂H₅—SO₂—CH₂—CH₂—CH₂— |
| 919. | OCClF₂ | (CH₃)₂N—CH₂—CH₂—CH₂— |
| 920. | OCClF₂ | (C₂H₅)₂N—CH₂—CH₂—CH₂— |
| 921. | OCClF₂ | CH₃—O—CH₂—C(CH₃)₂— |
| 922. | OCClF₂ | CH₃—S—CH₂—C(CH₃)₂— |
| 923. | OCClF₂ | CH₃—SO₂—CH₂—C(CH₃)₂— |
| 924. | OCClF₂ | C₂H₅—O—CH₂—C(CH₃)₂— |
| 925. | OCClF₂ | C₂H₅—S—CH₂—C(CH₃)₂— |
| 926. | OCClF₂ | C₂H₅—SO₂—CH₂—C(CH₃)₂— |
| 927. | OCClF₂ | (CH₃)₂N—CH₂—C(CH₃)₂— |
| 928. | OCClF₂ | (C₂H₅)₂N—CH₂—C(CH₃)₂— |

TABLE A-continued

| | R¹ | R² |
|---|---|---|
| 929. | OCClF$_2$ | [(CH$_3$)$_2$CH]$_2$N—CH$_2$—C(CH$_3$)$_2$— |
| 930. | OCClF$_2$ | Cl—CH$_2$—C≡C—CH$_2$— |
| 931. | OCClF$_2$ | CH$_3$—O—C(O)—CH$_2$ |
| 932. | OCClF$_2$ | C$_2$H$_5$—O—C(O)—CH$_2$ |
| 933. | OCClF$_2$ | CH$_3$—O—C(O)—CH(CH$_3$)— |
| 934. | OCClF$_2$ | C$_2$H$_5$—O—C(O)—CH(CH$_3$)— |
| 935. | OCClF$_2$ | (CH$_3$O)$_2$CH—CH$_2$— |
| 936. | OCClF$_2$ | (C$_2$H$_5$O)$_2$CH—CH$_2$— |

The following compounds of the formula (I), which can optionally be present in their isomeric formulae (I-A) and (I-B), are explicitly known from the publications cited at the start,

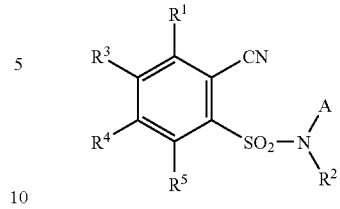

wherein R¹, R², R³, R⁵ have the meaning stated in table B and R⁴ and A mean hydrogen.

TABLE B

| Example No. | R³ | R⁵ | R¹ | R² | M.Pt. [° C.] |
|---|---|---|---|---|---|
| 1 | H | H | CH$_3$ | n-CH$_2$CH$_2$CH$_3$ | 74-77 |
| 2 | H | H | OCH$_3$ | —CH$_3$ | 121-128 |
| 3 | Cl | H | CH$_3$ | —CH$_2$CH$_3$ | 85-90 |
| 4 | CN | CH$_3$ | CH$_3$ | —CH$_3$ | 178-180 |
| 5 | Br | H | CH$_3$ | —CH$_2$CH$_3$ | 112-114 |
| 6 | Br | H | CH$_3$ | cyclopropyl | 140-142 |
| 7 | Br | H | CH$_3$ | n-C$_4$H$_9$ | 112-116 |
| 8 | Br | H | CH$_3$ | —CH(CH$_3$)$_2$ | 102-103 |
| 9 | Br | H | CH$_3$ | n-CH$_2$CH$_2$CH$_3$ | 119-120 |
| 10 | Br | H | CH$_3$ | C$_6$H$_5$—CH$_2$— | 139-140 |
| 11 | Br | H | CH$_3$ | 4-(CH$_3$)$_3$C—C$_6$H$_4$—CH$_2$— | 147-151 |
| 12 | H | H | CH$_3$ | C$_6$H$_5$—CH$_2$— | 117-119 |
| 13 | H | H | CH$_3$ | 4-(CH$_3$)$_3$C—C$_6$H$_4$—CH$_2$— | 97-103 |
| 14 | H | H | CH$_3$ | 4-Cl—C$_6$H$_4$—CH$_2$— | 150-151 |
| 15 | Br | H | CH$_3$ | 3-(CH$_3$O)—C$_6$H$_4$—CH$_2$— | 123-125 |
| 16 | H | H | CH$_3$ | 3-(CH$_3$O)—C$_6$H$_4$—CH$_2$— | 117-122 |
| 17 | Br | H | CH$_3$ | 4-(CH$_3$O)—C$_6$H$_4$—CH$_2$— | 156-161 |
| 18 | H | H | CH$_3$ | 4-(CH$_3$O)—C$_6$H$_4$—CH$_2$— | 127-132 |
| 19 | Br | H | CH$_3$ | 2-(CH$_3$O)—C$_6$H$_4$—CH$_2$— | 103-108 |
| 20 | H | H | CH$_3$ | 2-(CH$_3$O)—C$_6$H$_4$—CH$_2$— | 127-130 |
| 21 | Br | H | CH$_3$ | 4-Cl—C$_6$H$_4$—CH$_2$— | 127-131 |
| 22 | Br | H | CH$_3$ | 3-Cl—C$_6$H$_4$—CH$_2$— | 102-108 |
| 23 | H | H | CH$_3$ | 3-Cl—C$_6$H$_4$—CH$_2$— | 118-125 |
| 24 | Br | H | CH$_3$ | 2-Cl—C$_6$H$_4$—CH$_2$— | 118-125 |
| 25 | H | H | CH$_3$ | 2-Cl—C$_6$H$_4$—CH$_2$— | 128-131 |
| 26 | Br | H | CH$_3$ | 4-(F$_3$C)—C$_6$H$_4$—CH$_2$— | 153-155 |
| 27 | H | H | CH$_3$ | 4-(F$_3$C)—C$_6$H$_4$—CH$_2$— | 135-137 |
| 28 | Br | H | CH$_3$ | cyclopropyl-CH$_2$— | 106-110 |
| 29 | H | H | CH$_3$ | —CH$_3$ | 83-89 |
| 30 | H | H | CH$_3$ | —CH$_2$CH$_3$ | 98-103 |
| 31 | H | H | CH$_3$ | prop-2-ynyl | 104-107 |
| 32 | Br | H | CH$_3$ | —CH$_2$—CN | 106-110 |
| 33 | H | H | CH$_3$ | cyclopropyl-CH$_2$— | 89-93 |
| 34 | H | H | CH$_3$ | —CH$_2$—CN | 130-134 |
| 35 | Br | H | CH$_3$ | prop-2-ynyl | ¹H-NMR |
| 36 | Br | H | CH$_3$ | (CH$_3$)$_3$C—CH$_2$— | 112-114 |
| 37 | H | H | CH$_3$ | (CH$_3$)$_3$C—CH$_2$— | 86-93 |
| 38 | H | H | CH$_3$ | CH$_2$=CHCH$_2$— | ¹H-NMR |
| 39 | H | H | OCH$_3$ | —CH$_2$CH$_3$ | 121-126 |
| 40 | H | H | OCH$_3$ | C$_6$H$_5$—CH$_2$— | 108-119 |
| 41 | H | H | OCH$_3$ | —CH(CH$_3$)$_2$ | 104-113 |
| 42 | H | H | OCH$_3$ | prop-2-ynyl | 122-138 |
| 43 | H | H | OCH$_3$ | —CH$_2$—CN | ¹H-NMR |
| 44 | H | H | OCH$_3$ | CH$_2$=CHCH$_2$— | ¹H-NMR |
| 45 | H | H | OCH$_3$ | H | 186-198 |
| 46 | Cl | H | CH$_3$ | —CH$_3$ | 112-122 |
| 47 | Cl | H | CH$_3$ | H | 160-162 |
| 48 | H | H | OCH$_2$CH$_3$ | —CH$_3$ | 91-95 |
| 49 | H | H | OCH$_2$CH$_3$ | —CH$_2$CH$_3$ | 111-113 |
| 50 | H | H | OCH$_2$CH$_3$ | H | 183-186 |
| 51 | Cl | H | CH$_3$ | C$_6$H$_5$—CH$_2$— | 132-135 |
| 52 | Cl | H | CH$_3$ | —CH(CH$_3$)$_2$ | 86-94 |
| 53 | Cl | H | CH$_3$ | prop-2-ynyl | ¹H-NMR |
| 54 | Cl | H | CH$_3$ | H$_2$C=CHCH$_2$— | 95-96 |
| 55 | Cl | H | CH$_3$ | FH$_2$CCH$_2$— | 115-121 |
| 56 | H | H | OCH$_2$CH$_3$ | C$_6$H$_5$—CH$_2$— | oil |
| 57 | H | H | OCH$_2$CH$_3$ | prop-2-ynyl | 105-112 |
| 58 | H | H | OCH$_2$CH$_3$ | —CH$_2$—CN | 129-134 |

TABLE B-continued

| Example No. | $R^3$ | $R^5$ | $R^1$ | $R^2$ | M.Pt. [° C.] |
|---|---|---|---|---|---|
| 59 | H | H | $OCH_2H_3$ | $CH_2=CHCH_2—$ | oil |
| 60 | H | H | $OCH_2CH_3$ | $—CH_2—CH_2—CH_3$ | 113-115 |
| 61 | H | H | $OCH_2CH_3$ | cyclopropyl-$CH_2$ | 128-130 |
| 62 | Cl | H | $CH_3$ | $—CH_2—CN$ | 134-138 |
| 63 | H | H | $OCH_2CH_3$ | $—CH_2—CF_3$ | oil |
| 64 | H | H | $OCH_2CH=CH_2$ | $—CH_2—CH_3$ | oil |
| 65 | H | H | $OCH(CH_3)_2$ | $—CH_2—CH_3$ | oil |
| 66 | H | H | $OCHF_2$ | $—CH_2—CH_3$ | 98-100 |
| 67 | H | H | $OCH(CH_3)_2$ | H | 132-136 |
| 68 | H | H | $OCH(CH_3)_2$ | prop-2-ynyl | oil |
| 69 | H | H | $OCH(CH_3)_2$ | $—CH_2CN$ | oil |
| 70 | H | H | $OCH(CH_3)_2$ | cyclopropyl | oil |
| 71 | H | H | $OCH(CH_3)_2$ | $—CH(CH_3)_2$ | oil |
| 72 | H | H | $OCH(CH_3)_2$ | $C_6H_5—CH_2—$ | oil |
| 73 | H | H | $OCH(CH_3)_2$ | $—CH_2—CH_3$ | oil |
| 74 | Br | H | $CH_3$ | H | 149-151 |
| 75 | H | H | $CH_3$ | H | 171-174 |
| 76 | H | H | $OCH(CH_3)_2$ | $O—CH_2—CH_3$ | oil |
| 77 | H | H | $OCH(CH_3)_2$ | $—CH_2—CH_2—CH_3$ | oil |
| 78 | H | H | $OCHF_2$ | H | 135-137 |
| 79 | H | H | $OCHF_2$ | $—CH_2—C≡CH$ | 65-70 |
| 80 | H | H | $OCH_2CHClCH_2Cl$ | H | 123-129 |
| 81 | H | H | $OCH(CH_3)_2$ | $—CH_3$ | 82-91 |
| 82 | H | H | $OCH_3$ | $—CH_2$-c-$C_3H_5$ | 92-95 |
| 83 | H | H | $OCH_3$ | -c-$C_3H_5$ | 142-148 |
| 84 | H | H | $OCH_3$ | $—O—CH_2CH_3$ | 138-143 |
| 85 | H | H | $OCH_3$ | $—CH_2—CH_2—CN$ | 123-130 |
| 86 | H | H | $OCH_3$ | $—CH_2—CH_2—S—CH_3$ | oil |
| 87 | H | H | $OCH_3$ | $—CH_2—CH_2—S(O)_2—CH_3$ | 157-160 |
| 88 | H | H | $OCH_3$ | $—CH_2—CH_2F$ | 134-140 |
| 89 | H | H | $OCHF_2$ | H | 122-128 |
| 90 | H | H | $OCH_3$ | $—CH_2—CF_3$ | 136-141 |
| 91 | H | H | $OCH_3$ | $—CH_2—CHF_2$ | 116-118 |
| 92 | H | H | $OCH_3$ | $—O—CH_3$ | 136-139 |
| 93 | Br | H | $OCH_3$ | $—CH_2—C≡CH$ | 110-115 |
| 94 | H | H | $OCH_3$ | $—CH_2—CH_2—N(CH_3)_2$ | 94-97 |
| 95 | Br | H | $OCH_3$ | $—CH_2—C_6H_5$ | 134-136 |
| 96 | H | H | $OCHF_2$ | $—CH_2—CF_3$ | 120-138 |
| 97 | H | H | $OCHF_2$ | $—CH_2—C_6H_5$ | 115-117 |
| 98 | H | H | $OCHF_2$ | -c-$C_3H_5$ | 87-91 |
| 99 | H | H | $OCHF_2$ | $—CH_2—CH_2—S—CH_3$ | $^1$H-NMR |
| 100 | Br | H | $OCHF_2$ | $—CH_3$ | 168-173 |
| 101 | H | H | $OCHF_2$ | $—CH_2—CH=CH_2$ | 75-78 |
| 102 | H | H | $OCHF_2$ | $—CH_2$-c-$C_3H_5$ | $^1$H-NMR |
| 103 | H | H | $OCHF_2$ | $—CH_2—CH_2—CH_3$ | 54-58 |
| 104 | H | H | $OCHF_2$ | $—CH_2—CH_2—O—CH_3$ | $^1$H-NMR |
| 105 | H | H | $OCHF_2$ | $—CH_2—CH_2—CN$ | 83-88 |
| 106 | H | H | $OCHF_2$ | $—CH—(CH_3)_2$ | 72-74 |
| 107 | H | H | $OCHF_2$ | $—CH_2—CHF_2$ | 92-96 |
| 108 | H | H | $OCHF_2$ | $—O—CH_3$ | oil |
| 109 | H | H | $CF_3$ | $—CH_2—CH_3$ | 81-86 |
| 110 | H | H | $CF_3$ | $—CH_2—C≡CH$ | 106-111 |
| 111 | H | H | $CF_3$ | $—CH_2—C_6H_5$ | 106-108 |
| 112 | H | H | $CF_3$ | $—CH_3$ | 104-113 |
| 113 | H | H | $CF_3$ | $—CH_2—CH=CH_2$ | 71-73 |
| 114 | H | H | $CF_3$ | $—CH—(CH_3)_2$ | 65-67 |
| 115 | H | H | $CF_3$ | $—CH_2—CH_2—CH_3$ | 62-66 |
| 116 | H | H | $CF_3$ | $—CH_2$-c-$C_3H_5$ | oil |
| 117 | H | H | $CF_3$ | $—CH_2—CF_3$ | oil |
| 118 | H | H | $CF_3$ | $—CH_2—CH_2—S—CH_3$ | oil |
| 119 | H | H | $CF_3$ | -c-$C_3H_5$ | 94-96 |
| 120 | H | H | $CF_3$ | $—O—CH_2—CH_3$ | 118-120 |
| 121 | H | H | $CF_3$ | $—CH_2—CH_2—SO_2—CH_3$ | 169-171 |
| 122 | H | H | $CH_3$ | $—O—CH_2—CH_3$ | 118-121 |
| 123 | H | H | $CH_3$ | $—O—CH_3$ | 136-140 |
| 124 | H | H | $CH_3$ | cyclobutyl | HPLC/MS |
| 125 | H | H | $CH_3$ | cyclopentyl | HPLC/MS |
| 126 | H | H | $CH_3$ | cyclohexyl | HPLC/MS |
| 127 | H | H | $CH_3$ | cyclopropyl | HPLC/MS |
| 128 | H | H | $CH_3$ | $—C(CH_3)_2—CH_2—CH_3$ | HPLC/MS |
| 129 | H | H | $CH_3$ | $—CH_2—CH_2—CH_2—N(C_2H_5)_2$ | HPLC/MS |
| 130 | H | H | $CH_3$ | $—CH(CH_3)—CH(CH_3)_2$ | HPLC/MS |
| 131 | H | H | $CH_3$ | $—CH(CH_3)—C(CH_3)_3$ | HPLC/MS |
| 132 | H | H | $CH_3$ | $—C(CH_3)_3$ | HPLC/MS |
| 133 | H | H | $CH_3$ | $—C(CH_3)(C_2H_5)—CH_2—CH_3$ | HPLC/MS |
| 134 | H | H | $CH_3$ | $—C(CH_3)_2—CH_2—CH_2—CH_3$ | HPLC/MS |
| 135 | H | H | $CH_3$ | $—CH_2—CH_2—N[CH(CH_3)_2]_2$ | HPLC/MS |
| 136 | H | H | $CH_3$ | $—CH_2—CH_2—O—C_2H_5$ | HPLC/MS |

TABLE B-continued

| Example No. | R³ | R⁵ | R¹ | R² | M.Pt. [° C.] |
|---|---|---|---|---|---|
| 137 | H | H | CH₃ | —CH(C₂H₅)₂ | HPLC/MS |
| 138 | H | H | CH₃ | —CH(CH₃)—CH₂—CH(CH₃)₂ | HPLC/MS |
| 139 | H | H | CH₃ | —CH(C₂H₅)—CH₂—O—CH₃ | HPLC/MS |
| 140 | H | H | CH₃ | —C(CH₃)₂—C≡CH | HPLC/MS |
| 141 | H | H | CH₃ | —CH(CH₃)—CH₂—O—C₂H₅ | HPLC/MS |
| 142 | H | H | CH₃ | CH(CH₃)—CH₂—O—CH₃ | HPLC/MS |
| 143 | H | H | CH₃ | —CH₂—CH(CH₃)—C₂H₅ | HPLC/MS |
| 144 | H | H | CH₃ | —CH(CH₃)—CH₂—S—CH₃ | HPLC/MS |
| 145 | H | H | CH₃ | —CH₂—CH(OCH₃)₂ | ¹H-NMR |
| 146 | H | H | CH₃ | —CH₂—CH₂—C(CH₃)₃ | HPLC/MS |
| 147 | H | H | CH₃ | —CH₂—CH(OC₂H₅)₂ | HPLC/MS |
| 148 | H | H | CH₃ | —CH₂—CH₂—S—CH₃ | HPLC/MS |
| 149 | H | H | CH₃ | —CH₂—CH(CH₃)₂ | HPLC/MS |
| 150 | H | H | CH₃ | —CH₂—CH₂—CH(CH₃)₂ | HPLC/MS |
| 151 | H | H | CH₃ | —CH₂—CH₂—CH₂—O—CH₃ | HPLC/MS |
| 152 | H | H | CH₃ | —CH₂—CH(CH₃)—O—CH₃ | HPLC/MS |
| 153 | H | H | CH₃ | —CH₂—CH(CH₃)—CH₂C₂H₅ | HPLC/MS |
| 154 | H | H | CH₃ | —CH₂—CH₂—CH₂—S—CH₃ | HPLC/MS |
| 155 | H | H | CH₃ | —C(CH₃)₂—CH₂—S—C₂H₅ | HPLC/MS |
| 156 | H | H | CH₃ | —C(CH₃)₂—CH₂—S—CH₃ | HPLC/MS |
| 157 | H | H | CH₃ | —CH(CH₃)—CH₂—N(CH₃)₂ | HPLC/MS |
| 158 | H | H | CH₃ | —C(CH₃)(n-C₃H₇)₂—C≡CH | HPLC/MS |
| 159 | H | H | CH₃ | —C(CH₃)₂—CH=CH₂ | HPLC/MS |
| 160 | H | H | CH₃ | —CH(CH₃)—C(O)—O—CH₃ | HPLC/MS |
| 161 | H | H | CH₃ | —CH(CH₃)-c-C₃H₅ | HPLC/MS |
| 162 | H | H | CH₃ | —CH₂—CF₃ | HPLC/MS |
| 163 | H | H | CH₃ | —CH₂—CH₂—O—CH₃ | HPLC/MS |
| 164 | H | H | CH₃ | —CH(CH₃)—C₂H₅ | HPLC/MS |
| 165 | H | H | CH₃ | CH(CH₃)₂ | HPLC/MS |
| 166 | H | H | CH₃ | —C(CH₃)₂—CH₂—CN | HPLC/MS |
| 167 | H | H | CH₃ | —CH₂—CH₂—CH₂—N(CH₃)₂ | HPLC/MS |
| 168 | H | H | CH₃ | —CH₂—CH₂—CH₂—CH₂—CH₃ | HPLC/MS |
| 169 | H | H | CH₃ | —CH₂—CH₂—F | HPLC/MS |
| 170 | H | H | CH₃ | —CH₂—CH₂—CH₂—O—C₂H₅ | HPLC/MS |
| 171 | H | H | CH₃ | —CH₂—CH₂—O—CH(CH₃)₂ | HPLC/MS |
| 172 | H | H | CH₃ | —CH(CH₃)—CH₂—Cl | HPLC/MS |
| 173 | H | H | CH₃ | CH₂—CH₂—CH₂—Cl | HPLC/MS |
| 174 | H | H | CH₃ | —CH₂—C≡C—CH₂—Cl | HPLC/MS |
| 175 | H | H | CH₃ | —CH₂—C(O)—O—CH₃ | HPLC/MS |
| 176 | H | H | CH₃ | —CH₂—CH₂—CH₂—Br | HPLC/MS |
| 177 | H | H | CH₃ | —CH₂—CH₂—CH₂—CH₃ | HPLC/MS |
| 178 | H | H | CH₃ | —CH₂—CH₂—S—C₂H₅ | HPLC/MS |
| 179 | CN | H | CH₃ | —CH₂—CH₃ | 114-119 |
| 180 | CN | H | CH₃ | —CH₃ | 172-175 |
| 181 | CN | H | CH₃ | —CH₂—C≡CH | 95-105 |
| 182 | CN | H | CH₃ | H | oil |
| 183 | CN | H | CH₃ | —CH₂—CH=CH₂ | 83-95 |
| 184 | CN | H | CH₃ | —CH₂—CH₂—CH₃ | 95-99 |
| 185 | CN | H | CH₃ | —CH₂—CH₂—F | oil |
| 186 | CN | H | CH₃ | cyclopropyl | oil |
| 187 | CN | H | CH₃ | —O—CH₃ | 139-142 |
| 188 | OCH₃ | H | CH₃ | —CH₂—CH₃ | 171-174 |
| 189 | OCH₃ | H | CH₃ | —CH₂—C≡CH | 151-155 |
| 190 | OCH₃ | H | CH₃ | —H | 171-180 |
| 191 | OCH₃ | H | CH₃ | —CH₃ | 171-175 |
| 192 | H | Cl | CH₃ | CH₂CH₃ | 119-123 |
| 193 | H | Br | CH₃ | CH₂CH₃ | 141-144 |

Here M.Pt. means melting point c-C₃H₅: cyclopropyl, and n-C₃H₇: n-propyl

Furthermore, the following compounds of the formula (I) are explicitly known from the publications cited at the start,

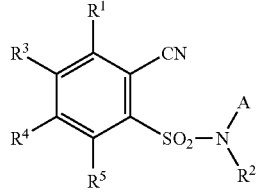
(I)

where A, $R^1$, $R^2$, $R^3$, $R^5$ have the meaning stated in table C and $R^4$ means hydrogen.

TABLE C

| Example No. | A | $R^2$ | $R^1$ | $R^3$ | $R^5$ | M.Pt. [° C.] |
|---|---|---|---|---|---|---|
| 194 | $C_2H_5$ | $C_2H_5$ | $OCH_3$ | H | H | 77-83 |
| 195 | $CH_2CH=CH_2$ | $CH_2CH=CH_2$ | $OCH_3$ | H | H | 60-73 |
| 196 | $CH_3$ | $CH_3$ | $OCH_3$ | Br | H | 75-80 |
| 197 | $CH_3$ | $CH_3$ | $OCH_3$ | H | $NO_2$ | oil |
| 198 | $CH_3$ | $C_2H_5$ | $OCHF_2$ | H | H | oil |
| 199 | $CH_3$ | $CH_3$ | $OCH_3$ | H | $NH_2$ | oil |
| 200 | $C_2H_5$ | $C_2H_5$ | $OCHF_2$ | H | H | oil |
| 201 | $CH_3$ | $CH_3$ | $OC_2H_5$ | H | H | 86-94 |
| 202 | $C_2H_5$ | $C_2H_5$ | $OC_2H_5$ | H | H | oil |
| 203 | $CH_3$ | $CH_3$ | $OCH(CH_3)_2$ | H | H | oil |
| 204 | $CH_3$ | $CH_3$ | $OCH_2CHClCH_2Cl$ | H | H | oil |
| 205 | $CH_3$ | $CH_3$ | $OCF_2-Cl$ | H | H | 83-85 |
| 206 | $CH_3$ | $CH_3$ | $OCF_3$ | H | H | 95-98 |
| 207 | $CH_3$ | $C_2H_5$ | $OCF_3$ | H | H | oil |
| 208 | $C_2H_5$ | $C_2H_5$ | $OCF_3$ | H | H | oil |
| 209 | $CH_3$ | $C_2H_5$ | $OCF_2Cl$ | H | H | oil |
| 210 | $C_2H_5$ | $C_2H_5$ | $OCF_2Cl$ | H | H | oil |
| 211 | $CH_3$ | $CH_3$ | $OCH_3$ | H | $CH_3$ | 89-93 |
| 212 | $CH_3$ | $GH_3$ | $OCH_3$ | H | $C_2H_5$ | 138-140 |
| 213 | $CH_3$ | $CH_3$ | $OCH_3$ | H | $CH_3OCO$ | 134-138 |
| 214 | $CH_3$ | $CH_3$ | $OCH_3$ | H | Cl | LC/MS |
| 215 | $CH_3$ | $CH_3$ | $OCH_3$ | H | H | $^1$H-NMR |
| 216 | $CH_3$ | $C_2H_5$ | $OCF_2-CHFCl$ | H | H | $^1$H-NMR |
| 217 | $CH_3$ | $CH_3$ | $OCH_3$ | H | F | 123-125 |
| 218 | $CH_3$ | $C_2H_5$ | $OCH_3$ | H | F | $^1$H-NMR |
| 219 | $CH_3$ | $CH(CH_3)_2$ | $OCH_3$ | H | F | $^1$H-NMR |
| 220 | $CH_3$ | $CH_2C\equiv CH$ | $OCH_3$ | H | F | $^1$H-NMR |
| 221 | $CH_3$ | $CH_3$ | $OCH_3$ | $OCH_3$ | H | $^1$H-NMR |
| 222 | $CH_3$ | $CH_3$ | $OCHF_2$ | H | F | 102-105 |
| 223 | $CH_3$ | $CH_3$ | $OCH_3$ | Cl | Br | 93-98 |
| 224 | $CH_3$ | $CH_3$ | $OCH_3$ | F | H | $^1$H-NMR |
| 225 | $CH_3$ | $CH_2-CH=CH_2$ | $OCH_3$ | H | H | |

Here, M.Pt. = melting point.

Some of the compounds set out in table B and C are characterized by $^1$H NMR or by LC-MS. The results are set out in WO 2005/035486 and WO 2006/056433. Reference is hereby expressly made to the content of these publications.

Further, the following compound of the formula (I-226) and isomeric forms thereof I-226-A and I-226-B are explicitly known from the publications cited at the start,

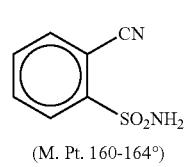
(I-226)
(M. Pt. 160-164°)

Examples 225 and 42-A are characterized by $^1$H NMR. The signals are defined by a chemical shift (in ppm) relative to tetramethylsilane, by their multiplicity and their integral, the number of hydrogen atoms corresponding thereto being stated in the brackets in each case. Here m means multiplet, t triplet, d doublet and s singlet. The results are set out below:

EX. 225

$^1$H-NMR (400 mHz, $d_6$-DMSO: δ=2.77 ppm (s, 3H, $NCH_3$); 3.82-3.81 ppm (d, 2H, N—$CH_2$); 4.00 ppm (s, 3H, $OCH_3$); 5.19-5.27 ppm (m, 2H, CH=$CH_2$); 5.68-5.78 ppm (m, 1H, CH=$CH_2$); 7.56-7.58 ppm (2H, CH); 7.83-7.87 ppm (1H, CH).

EX. 42-A $^1$H-NMR (400 mHz, $d_6$-DMSO: δ=9.20 ppm (1H, =NH); 7.91-7.88 (1H, CH); 7.73-7.71 ppm (1H, CH); 7.61-7.60 (1H, CH); 4.52 ppm (2H, N—$CH_2$); 4.07 ppm (3H, O—$CH_3$); 3.28 ppm (t, 1H, C≡CH).

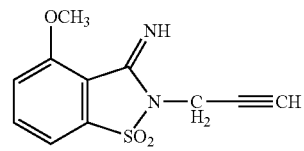
(42-A)

EXAMPLE A

Activity Increase Due to Ammonium Salts

*Myzus persicae*—Test (MYZUPE)

| Solvent: | 7 parts by weight of dimethylformamide |
|---|---|
| Emulsifier: | 2 parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts is necessary, these are in each case pipetted into the finished preparation solution in a concentration of 1000 ppm after dilution.

Paprika plants (*Capsicum annuum*) which are severely infested by the green peach aphid (*Myzus persicae*) are treated by spraying with the active substance preparation in the desired concentration.

After the desired time, the kill rate in % is determined. Here 100% means that all the animals were killed; 0% means that no animals were killed.

TABLE A

| Active substance | Active substance ppm | Kill rate/% after 6 days a.i. | +AS (1000 ppm) |
|---|---|---|---|
| 42 | 20 | 5 | 20 |
| 42-A | 20 | 0 | 45 |
| 45-B* | 4 | 35 | 60 |

AS = ammonium sulfate
*known from EP 33984, Ex. 33

(45-B)

EXAMPLE B

Activity Increase Due to Ammonium Salts

*Aphis gossypii*-Test (APHIGO)

| Solvent: | 7 parts by weight of dimethylformamide |
|---|---|
| Emulsifier: | 2 parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts is necessary, these are in each case pipetted into the finished preparation solution in a concentration of 1000 ppm after dilution.

Cotton leaves (*Gossypium hirsutum*) which are severely infested with the cotton aphid (*Aphis gossypii*) are sprayed with an active substance preparation with the desired concentration.

After the desired time, the kill rate in % is determined. Here 100% means that all the aphids were killed; 0% means that no aphids were killed.

TABLE B

| Active substance | Active substance ppm | Kill rate/% after 6 days a.i. | +AS (1000 ppm) |
|---|---|---|---|
| 42-A | 20 | 30 | 98 |
| 42-A | 4 | 15 | 55 |
| 44 | 4 | 5 | 25 |
| 225 | 20 | 35 | 75 |

AS = ammonium sulfate

EXAMPLE C

Activity Increase Due to Ammonium Salts in Combination with Penetration Enhancers

*Myzus persicae*—Test (MYZUPE)

| Solvent: | 7 parts by weight of dimethylformamide |
|---|---|
| Emulsifier: | 2 (table C1)/1 (table C2) parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts, penetration enhancers or ammonium salts and penetration enhancers is necessary, these are in each case pipetted into the finished preparation solution in a concentration of 1000 ppm after dilution.

Paprika plants (*Capsicum annuum*) which are severely infested with the green peach aphid (*Myzus persicae*) are treated by spraying with the active substance preparation in the desired concentration.

After the desired time, the kill rate in % is determined. Here 100% means that all the animals were killed; 0% means that no animals were killed.

TABLE C1

| | | Kill rate/% after 6 days | | |
|---|---|---|---|---|
| Active substance | Active substance ppm | a.i. | +AS (1000 ppm) | +RME (1000 ppm) | +RME + AS (each 1000 ppm) |
| 42 | 100 | 75 | 80 | 99 | 100 |
| 42 | 20 | 5 | 20 | 25 | 70 |
| 42-A | 20 | 0 | 45 | 90 | 98 |
| 226 | 20 | 10 | 10 | 25 | 50 |
| 44 | 20 | 85 | 70 | 85 | 98 |
| 44 | 4 | 10 | 15 | 20 | 30 |
| 225 | 4 | 0 | 0 | 5 | 35 |

RME = rape oil methyl ester (formulated as 500 EW, concentration stated in g active substance/l)
AS = ammonium sulfate

TABLE C2

| Active substance | Active substance g/ha | a.i. | +AS (1000 ppm) | +RME (1000 ppm) | +RME + AS (each 1000 ppm) |
|---|---|---|---|---|---|
| 83 | 60 | 0 | 0 | 10 | 75 |
| 215 | 60 | 0 | 20 | 40 | 75 |
| 40 | 60 | 0 | 0 | 40 | 50 |

AS = ammonium sulfate
RME = rape oil methyl ester

EXAMPLE D

Activity Increase Due to Ammonium Salts in Combination with Penetration Enhancers

*Aphis gossypii*-Test (APHIGO)

| Solvent: | 7 parts by weight of dimethylformamide |
|---|---|
| Emulsifier: | 2 (table D1)/1 (table D2) parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts, penetration enhancers or ammonium salts and penetration enhancers is necessary, these are in each case pipetted into the finished preparation solution in a concentration of 1000 ppm after dilution.

Cotton leaves (*Gossypium hirsutum*) which are severely infested with the cotton aphid (*Aphis gossypii*) are sprayed with an active substance preparation with the desired concentration.

After the desired time, the kill rate in % is determined. Here 100% means that all the aphids were killed; 0% means that no aphids were killed.

TABLE D1

| Active substance | Active substance ppm | a.i. | +AS (1000 ppm) | +RME (1000 ppm) | +RME + AS (each 1000 ppm) |
|---|---|---|---|---|---|
| 226 | 4 | 20 | 20 | 35 | 55 |
| 226 | 0.8 | 0 | 0 | 20 | 35 |
| 44 | 4 | 5 | 25 | 45 | 55 |

RME = rape oil methyl ester (formulated as 500 EW, concentration stated in g active substance/l)
AS = ammonium sulfate

TABLE D2

| Active substance | Active substance g/ha | a.i. | +RME (1000 ppm) | +AS (1000 ppm) | +RME + AS (each 1000 ppm) |
|---|---|---|---|---|---|
| 83 | 2.4 | 10 | 30 | 55 | 85 |
| 41 | 2.4 | 50 | 10 | 80 | 93 |

AS = ammonium sulfate
RME = rape oil methyl ester

EXAMPLE E

Activity Increase Due to Ammonium Salts

*Tetranychus*-Test (OP-Resistant)

| Solvent: | 7 parts by weight of dimethylformamide |
|---|---|
| Emulsifier: | 2 parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts is necessary, these are in each case pipetted into the finished preparation solution in a concentration of 1000 ppm after dilution.

Bean plants (*Phaseolus vulgaris*) which are severely infested by all stages of the common spider mite (*Tetranychus urticae*) are treated by spraying with the active substance preparation in the desired concentration.

After the desired time, the kill rate in % is determined. here 100% means that all the spider mites were killed; 0% means that no spider mites were killed.

TABLE E

| Active substance | Active substance ppm | Kill rate/ % after 6 days | |
|---|---|---|---|
| | | a.i. | +AS (1000 ppm) |
| 44 | 20 | 40 | 70 |
| 225 | 20 | 20 | 80 |

AS = ammonium sulfate

EXAMPLE F

Activity Increase Due to Ammonium Salts in Combination with Penetration Enhancers

*Tetranychus*-Test (OP-Resistant)

| Solvent: | 7 parts by weight of dimethylformamide |
|---|---|
| Emulsifier: | 2 parts by weight of alkylaryl polyglycol ether |

For the preparation of a suitable active substance preparation, 1 part by weight of active substance is mixed with the stated quantities of solvent and emulsifier and the concentrate is diluted to the desired concentration with emulsifier-containing water. When addition of ammonium salts, penetration enhancers or ammonium salts and penetration enhancers is necessary, these are in each case pipetted into the finished preparation solution in a concentration of 1000 ppm after dilution.

Bean plants (*Phaseolus vulgaris*) which are severely infested by all stages of the common spider mite (*Tetranychus urticae*) are treated by spraying with the active substance preparation in the desired concentration.

After the desired time, the kill rate in % is determined. here 100% means that all the spider mites were killed; 0% means that no spider mites were killed.

TABLE F

| Active substance | Active substance ppm a.i. | +AS (1000 ppm) | +RME (1000 ppm) | +RME + AS (each 1000 ppm) |
|---|---|---|---|---|
| 42-A | 4 | 70 | 50 | 75 | 95 |
| 42-A | 0.8 | 50 | 30 | 45 | 80 |
| 226 | 20 | 50 | 70 | 60 | 90 |

Kill rate/% after 6 days

RME = rape oil methyl ester (formulated as 500 EW, concentration stated in g active substance/l)
AS = ammonium sulfate

The invention claimed is:

1. A composition comprising at least one insecticidal and/or acaricidal active substance of the 2-cyanobenzene-sulfonamide class of general formula (I) and isomeric forms thereof

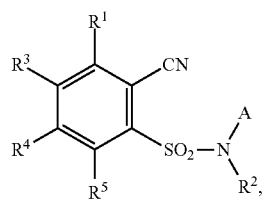

(I)

in which

A stands for hydrogen, $C_1$-$C_6$ alkyl or $C_2$-$C_6$ alkenyl;

$R^1$ stands for hydrogen, halogen, $C_1$-$C_4$ alkyl, $C_1$-$C_4$ haloalkyl, $C_1$-$C_4$ alkoxy or $C_1$-$C_4$ haloalkoxy;

$R^2$ stands for hydrogen, or stands for $C_1$-$C_6$ alkyl, $C_2$-$C_6$ alkenyl, $C_2$-$C_6$ alkynyl, $C_3$-$C_8$ cycloalkyl or $C_1$-$C_4$ alkoxy, each of which is unsubstituted, partially or completely halogenated and/or optionally bears one, two or three residues selected from the group consisting of $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_1$-$C_4$ alkoxycarbonyl, cyano, amino, ($C_1$-$C_4$ alkyl)amino, di-($C_1$-$C_4$ alkyl)amino, $C_3$-$C_8$ cycloalkyl and phenyl, wherein the phenyl is unsubstituted, partially or completely halogenated and/or optionally bears one, two or three substituents selected from the qroup consisting of $C_1$-$C_4$ alkyl, $C_1$-$C_4$ haloalkyl, $C_1$-$C_4$ alkoxy and $C_1$-$C_4$ haloalkoxy; and $R^3$, $R^4$ and $R^5$ independently stand for hydrogen, halogen, cyano, nitro, $C_1$-$C_6$ alkyl, $C_3$-$C_8$ cycloalkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_2$-$C_6$ alkenyl, $C_2$-$C_6$ alkynyl, $C_1$-$C_4$ alkoxycarbonyl, amino, ($C_1$-$C_4$ alkyl)amino, di-($C_1$-$C_4$ alkyl)amino, aminocarbonyl, ($C_1$-$C_4$ alkyl)aminocarbonyl or di-($C_1$-$C_4$ alkyl)aminocarbonyl, ammonium sulfate;

at least one penetration enhancer, wherein the penetration enhancer is rape oil methyl ester.

2. The composition as claimed in claim 1, wherein the active substance is a 2-cyanobenzenesulfonamide of the isomeric form (I-A)

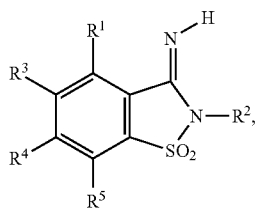

(I-A)

in which $R^1$ stands for hydrogen, halogen, $C_1$-$C_4$ alkyl, $C_1$-$C_4$ haloalkyl, $C_1$-$C_4$ alkoxy or $C_1$-$C_4$ haloalkoxy;

$R^2$ stands for $C_1$-$C_6$ alkyl, $C_2$-$C_6$ alkenyl, $C_2$-$C_6$ alkynyl, $C_3$-$C_8$ cycloalkyl or $C_1$-$C_4$ alkoxy, each of which is unsubstituted, partially or completely halogenated and/or optionally bears one, two or three residues selected from the group consisting of $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_1$-$C_4$ alkoxycarbonyl, cyano, amino, ($C_1$-$C_4$ alkyl)amino, di-($C_1$-$C_4$ alkyl) amino, $C_3$-$C_8$ cycloalkyl and phenyl, wherein the phenyl is unsubstituted, partially or completely halogenated and/or optionally bears one, two or three substituents selected from the group consisting of $C_1$-$C_4$ alkyl, $C_1$-$C_4$ haloalkyl, $C_1$-$C_4$ alkoxy and $C_1$-$C_4$ haloalkoxy; and $R^3$, $R^4$ and $R^5$ independently stand for hydrogen, halogen, cyano, nitro, $C_1$-$C_6$ alkyl, $C_3$-$C_8$ cycloalkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_2$-$C_6$ alkenyl, $C_2$-$C_6$ alkynyl, $C_1$-$C_4$ alkoxycarbonyl, amino, ($C_1$-$C_4$ alkyl)amino, di-($C_1$-$C_4$ alkyl)amino, aminocarbonyl, ($C_1$-$C_4$ alkyl)aminocarbonyl or di-($C_1$-$C_4$ alkyl)aminocarbonyl.

3. The composition as claimed in claim 1, wherein the active substance is between 0.5 and 50% by weight.

4. The composition as claimed in claim 1, wherein said composition comprises between 0.5 and 80 mmol/l of ammonium sulfate.

5. The composition as claimed in claim 1, wherein the content of penetration enhancer is between 1 and 95% by weight.

6. A method for controlling noxious insects and/pr spider mites, comprising applying an effective amount of a composition as claimed in claim 1, either undiluted or diluted, onto said insects and/or spider mites or their habitat.

7. A method for increasing the action of pesticides containing an active substance of the 2-cyanobenzenesulfonamide class of general formula (I) and/or isomeric form (I-A) as claimed in claim 1 or claim 2, comprising preparing a ready-to-use spray comprising said pesticides, ammonium sulfate, and at least said one penetration enhancer that is rape oil methyl ester.

8. The method as claimed in claim 7, wherein the penetration enhancer is present in a final concentration of 0.1 to 10 g/l and/or the ammonium sulfate is present in a final concentration of 0.5 to 80 mmol/l.

9. The composition of claim 1, wherein said 2-cyanobenzene-sulfonamide has the formula:

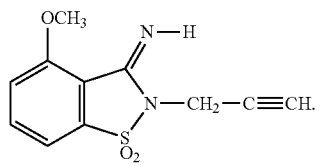

10. The composition of claim 9, wherein the penetration enhancer is present in a final concentration of 0.1 to 10 g/l and ammonium sulfate is present in a final concentration of 0.5 to 80 mmol/l.

11. The composition of claim 9, wherein said 2-cyanobenzene-sulfonamide is present in a concentration of 0.1 to 50 wt %.

\* \* \* \* \*